United States Patent
Dabney et al.

(10) Patent No.: US 6,633,658 B1
(45) Date of Patent: Oct. 14, 2003

(54) SYSTEM AND METHOD FOR MANAGING INTERMITTENT INTERFERENCE ON IMAGING SYSTEMS

(75) Inventors: James H. Dabney, Irvine, CA (US); Richard L. Quick, Mission Viejo, CA (US)

(73) Assignee: SenoRx, Inc., Aliso Viejo, CA (US)

(*) Notice: Subject to any disclaimer, the term of this patent is extended or adjusted under 35 U.S.C. 154(b) by 0 days.

(21) Appl. No.: 09/527,868

(22) Filed: Mar. 17, 2000

(51) Int. Cl.[7] .................................................. G06K 9/00
(52) U.S. Cl. ...................................... 382/128; 382/275
(58) Field of Search ................................ 382/100, 128, 382/131, 134, 254, 255, 260–266, 312; 600/439, 441, 453; 128/662.03–662.06; 324/322; 378/91, 98.11, 7

(56) References Cited

U.S. PATENT DOCUMENTS

| | | | |
|---|---|---|---|
| 4,517,976 A | | 5/1985 | Murakoshi et al. |
| 4,917,097 A | * | 4/1990 | Proudian et al. ........ 128/662.06 |
| 5,056,503 A | | 10/1991 | Nagasaki et al. |
| 5,269,289 A | * | 12/1993 | Takehana et al. .............. 128/4 |
| 5,543,831 A | * | 8/1996 | Tsuji et al. ..................... 348/65 |
| 5,545,942 A | | 8/1996 | Jaster et al. ................. 310/341 |
| 5,735,282 A | * | 4/1998 | Hossack ................. 128/662.03 |
| 5,788,636 A | | 8/1998 | Curley |
| 5,828,216 A | * | 10/1998 | Tschudin et al. ........... 324/322 |
| 5,840,030 A | | 11/1998 | Petric et al. ................ 600/439 |
| 5,860,927 A | * | 1/1999 | Sakaguchi et al. .......... 600/453 |
| 5,921,931 A | * | 7/1999 | O'Donnell et al. .......... 600/441 |
| 6,009,755 A | * | 1/2000 | Manome et al. .............. 73/602 |
| 6,019,725 A | * | 2/2000 | Vesely et al. ............... 128/916 |

FOREIGN PATENT DOCUMENTS

| | | |
|---|---|---|
| GB | 0429204 A1 | 1/1990 |
| GB | 2261379 A | 10/1992 |

OTHER PUBLICATIONS

Ishikawa et al., "Full–circular Surface Acoustic Wave Excitation for High Resolution Acoustic Microscopy Using Spherical Lens and Time Gate Technology", IEEE Transactions on Ultrasonics, vol. 46, No. 1, Jan. 1999, pp. 41–46.*

* cited by examiner

Primary Examiner—Jayanti K. Patel
(74) Attorney, Agent, or Firm—Duane Morris LLP

(57) ABSTRACT

A system and method for managing, reducing, or eliminating the deleterious effects of the operation of energy emitting instruments on imaging systems. The system and method of the invention can be built into the structure of an imaging system, or can be configured to adapt to existing imaging systems. An embodiment of a system incorporating features of the invention has an interference bar detector coupled to an interference bar acquisition device which relays information regarding a bar of interference to a processor which identifies the position and velocity of the interference bar moving across an image frame or image display. Based on the position and velocity of the interference bar within the image frame, the processor then computes the necessary corrections to the gating and timing of the operation of the energy emitting instrument so as to fix the position of the interference bar at a perimeter of the image display. In another embodiment, a portion of an image frame which contains interference from the operation of an energy emitting instrument can be replaced with a corresponding portion of another image frame which is clear of interference. The invention allows for such replacement of interference scrambled portions of an image frame to occur without undue interruption of the continuous image frame generation, video stream or video display output of the imaging system.

32 Claims, 36 Drawing Sheets

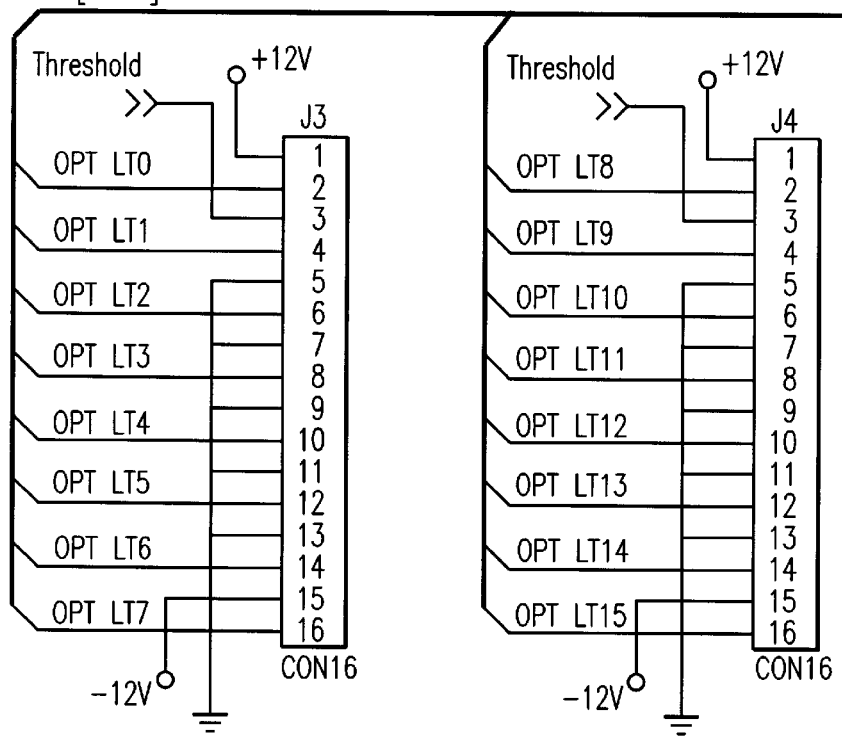
FIG. 20A
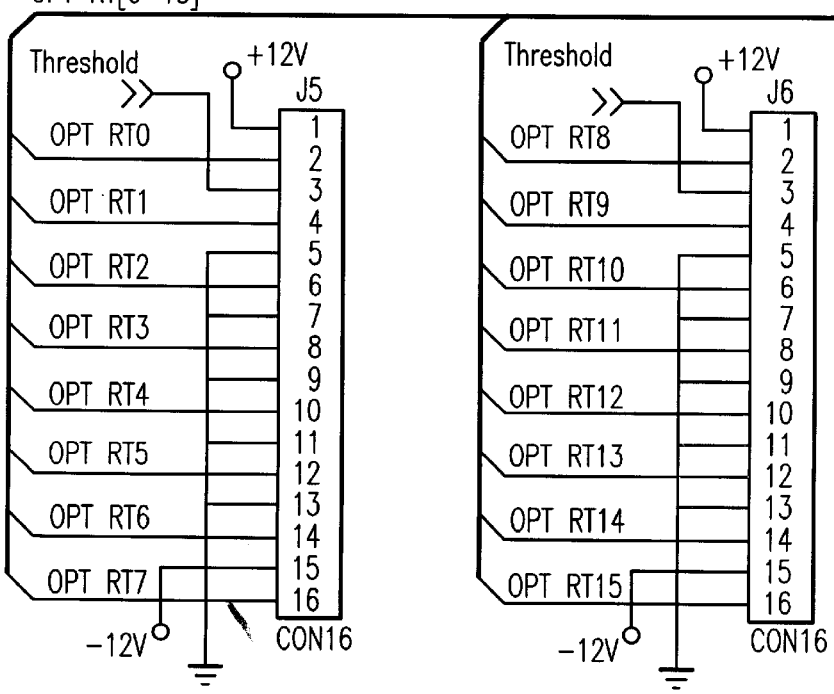

SYSTEM AND METHOD FOR MANAGING INTERMITTENT INTERFERENCE ON IMAGING SYSTEMS

BACKGROUND

The present invention relates generally to the field of imaging systems, specifically, medical imaging systems, and more specifically, ultrasonic imaging systems used in conjunction with electrosurgical biopsy instruments and methods.

In diagnosing and treating certain medical conditions, such as potentially cancerous tumors, it may be desirable to perform a biopsy, in which a specimen of the suspicious tissue is removed for pathological examination and analysis. In many instances, the suspicious tissue is located in a subcutaneous site, such as inside a human breast. To minimize surgical intrusion into patient's body, it is often desirable to insert a small instrument into the body for extracting the biopsy specimen while imaging the procedure using x-ray, stereotactic x-ray, digital x-ray, fluoroscopy, ultrasonic imaging, MRI or any other suitable form of imaging technique.

Electrosurgical techniques have been used in a variety of circumstances, including certain types of biopsy procedures. In electrosurgery, high frequency electrical energy is applied through a primary electrode to patient tissue. The electrical energy flows through the tissue to a return electrode that is in contact with the patient's tissue in monopolar electrosurgical systems. In bipolar electrosurgical systems, the electrical energy flows through the tissue from a primary electrode to a secondary electrode which is normally located on the same instrument as the primary electrode. Typically, the return electrode in monopolar systems is attached to the patient at a point remote from where the primary electrode contacts the tissue. The tissue adjacent the primary electrode can be ablated in order to form an opening in order to gain access to the tissue of interest. Thereafter, the tissue of interest can be ablated or cut with an electrosurgical electrode or any other suitable form of cutter in order to isolate a portion of the tissue of interest. Once the tissue of interest is isolated from surrounding tissue, it can be destroyed in situ, or can be removed for further analysis. An electrosurgical biopsy instrument is disclosed and claimed in U.S. patent application Ser. No. 09/159,467 for "Electrosurgical Biopsy Device and Method," assigned to the assignee of the subject application, and which is hereby incorporated by reference in its entirety.

During such a procedure, it is critical to accurately access the precise location of the suspicious tissue within the patient's body and to cut or isolate the suspicious tissue with precision so as to minimize trauma to surrounding healthy tissue. In order to accomplish this, it is generally necessary to accurately image the tissue of interest and surrounding tissue while the biopsy or surgical instrument is being positioned and activated. This gives the operator of the instrument visual feedback as to the relative position of the biopsy or surgical and suspicious tissue.

Ultrasonic imaging is frequently used to image the tissue of interest at the site of interest during a surgical or biopsy procedure. For example, during a breast biopsy procedure, the biopsy device is often imaged with ultrasonic imaging while the device is being inserted into the patient's breast and activated to remove or isolate a sample of suspicious breast tissue. If the biopsy device is an electrosurgical device, this can be problematic because radiated electrical and electromagnetic noise from the electrosurgical probe creates noise and interference within the ultrasound image and video display of the image. The interference is typically so severe that the sonogram produced by the ultrasonic imaging system during the operation of an electrosurgical device is completely obscured. Thus, the operator is in effect blinded as to the relative position of the electrosurgical device and suspicious tissue at the most critical moments of the procedure, i.e., when the device is being advanced into tissue or activated to remove or isolate tissue.

Previous methods for dealing with the interference created by operation of an electrosurgical generator (ESG) used to power an electrosurgical device have consisted essentially of gating the operation of the ultrasonic imaging system and the operation of the ESG in a mutually exclusive sequence. That is, the ultrasonic imaging system is gated to be operated only when the ESG is not operating and vice versa. In this way, the ESG operation never interferes with the imaging process of the ultrasonic imaging system. However, this method can be difficult and expensive to adapt to an existing ultrasonic imaging system because it can require modification of the internal operation of the ultrasonic imaging system. Although new ultrasonic imaging systems could be manufactured to have such a feature built into the system, there are vast numbers of ultrasonic imaging systems currently in place and replacement of these expensive existing systems would not be practical.

In addition, mutually exclusive operation of an ESG and ultrasonic imaging system in a gated sequence may not leave sufficient time for an effective period and duty factor of operation of the electrosurgical device. Most electrosurgical instruments must be in active radiofrequency emitting mode for a minimum actual time and minimum percentage of time during use or the instrument will not effectively ablate, cut, cauterize or otherwise treat the target tissue. In addition, the ultrasonic imaging system must be actively transmitting and receiving imaging signals for a sufficient percentage of time while the operator is attempting to image a desired area in order to produce a useable image.

What has been needed is a system and method to manage, reduce or eliminate imaging system interference caused by operation of an energy emitting surgical or biopsy instrument wherein the system allows for effective contemporaneous use of the imaging system and energy emitting instrument. What has also been needed is such a system and method which can be readily adapted to existing imaging systems without the need for expensive and cumbersome modifications of the existing imaging systems.

SUMMARY

The invention is directed generally to a system and method for managing, reducing, or eliminating the interference effects produced by the operation of interference signal generating devices in the vicinity of image signal receivers. Specifically, the invention is directed to a system for reducing the effects of electrosurgical interference on ultrasonic imaging systems when both are being operated simultaneously.

One embodiment of the invention is directed to an interference reduction system having a sync detector configured for communication with the imaging system and an interference bar detector in communication with the imaging system. A processor is in communication with the sync detector and interference bar detector. The processor is configured to calculate the position of an interference bar embedded within imaging system data from data collected by the interference bar detector. A gating and time base generator is in communication with the processor and is configured for communication with and gating of the energy emitting instrument. In a particular embodiment of the invention, the energy emitting instrument consists of an electrosurgical probe and the imaging system consists of an ultrasonic imaging system. The processor can be configured to gate the energy emitting instrument during periods of an imaging cycle corresponding to a desired portion of the image frame. The desired portion of the image frame is preferably a lateral edge of the image frame.

The interference bar detector can be a video monitor having a screen and a plurality of optical sensors in optical communication with the screen. The optical detectors are preferably photodiodes mounted in at least one linear array on the screen of the video monitor. An image enhancer may be disposed between and in electrical communication with the imaging system and video monitor in order to enhance the image data produced by the ultrasonic imaging system and enable the interference bar detector to more accurately detect an interference bar embedded in image data of the ultrasonic imaging system. In another embodiment, the interference bar detector can consist of a frame buffer in communication with the processor where the processor is configured to analyze pixels in a desired region of an image frame of imaging system data to determine whether an interference bar exists within the image frame.

In yet another embodiment of an interference reduction system, an image digitizer is configured for electrical communication with the imaging system and a processor. The processor has a frame buffer configured to store at least two image frames and which is configured to replace an interference scrambled portion of a first image frame stored in the frame buffer with a corresponding portion clear of interference from a second image frame stored in the frame buffer. A counter timer is in communication with the processor and configured to be electrically coupled to and gate the energy emitting instrument. Preferably, the energy emitting instrument consists of an electrosurgical probe and the imaging system is an ultrasonic imaging system. The processor can be configured to gate the energy emitting instrument during periods of an imaging cycle corresponding to a desired portion of the image frame which alternates position within sequential image frames so as to facilitate the replacement of interference scrambled portions within adjacent or near adjacent image frames.

In use, an embodiment of an interference reduction system manages intermittent interference imposed upon an imaging system during operation of the imaging system by gating the intermittent interference in frequency and phase to position interference scrambled portions of the imaging system data away from a desired portion of a display screen. In one embodiment, the intermittent interference is generated by an energy emitting instrument and gating of the interference is carried out by gating the operation of the energy emitting instrument. Preferably, the desired portion of the display screen is the middle of the display screen or a lateral edge or edges of the display screen.

Another embodiment of an interference reduction system manages intermittent interference of an imaging system produced by an energy emitting instrument by storing at least a first and second image frame produced by the imaging system into a frame buffer of the interference reduction system. The interference reduction system then replaces an interference scrambled portion of the first image frame with a corresponding second image frame portion that is clear of interference to produce a synthesized image frame that is substantially clear of interference. The synthesized image frame can then be displayed on a video display monitor. The first and second image frames can be temporally sequential in the frame buffer, or can be separated by one or more image frames. In addition, the first image frame can temporally precede the second image frame in the frame buffer or the second image frame may temporally precede the first image frame.

In a particular embodiment, the scrambled interference portion of the first image frame comprises an interference bar generated by an energy emitting instrument. Optionally, the energy emitting instrument can be gated in frequency and phase to position the interference bar of the image frame into a desired location within the image frame prior to replacing the interference bar of the first image frame with a corresponding second image frame portion that is clear of interference.

These and other advantages of the invention will become more apparent from the following detailed description when taken in conjunction with the accompanying drawings.

DETAILED DESCRIPTION

As discussed above, energy emitting instruments, such as electrosurgical generators, can often produce or emit intermittent interference energy in the form of signals and noise which produce intermittent interference in the images produced by imaging systems, such as ultrasonic imaging systems. It is desirable to have an interference reduction system which can be readily adapted to existing imaging systems available commercially. The phrase "interference reduction system" as used herein is meant to encompass any system or method having features of the invention which is capable of manipulating, reducing or managing interference of the visual display of imaged data. The term "intermittent interference" as used herein can encompass any form of noncontinuous interference. Intermittent interference can be periodic and occur at regular intervals, such as when the interference is produced by a gated or pulsed energy emitting device. Alternatively, intermittent interference can occur randomly or sporadically. Some of the embodiments of the invention described herein completely eliminate intermittent interference from the display of imaged data viewed by the user. Other embodiments of the invention described herein control and manipulate intermittent interference seen on the display of imaged data so as to manage or minimize the impact of the interference on the usefulness of the displayed image data.

The embodiments of the invention described herein are generally configured for adaptation to ultrasonic imaging systems designed for medical use to eliminate, manage or reduce interference caused by operation of electro surgical generators. However, the various embodiments of the systems and methods of the invention can be readily adapted to use on any type of imaging system, such as x-ray, digital x-ray, fluoroscopy, mammography, stereotactic x-ray, MRI, or the like, which is susceptible to intermittent interference energy from an energy emitting source. Examples of such energy emitting sources include equipment lasers, ultrasonic interventional tools such as lithotripsy devices, or any other source of sonic, electric, magnetic or electromagnetic interference noise.

Figure 1:
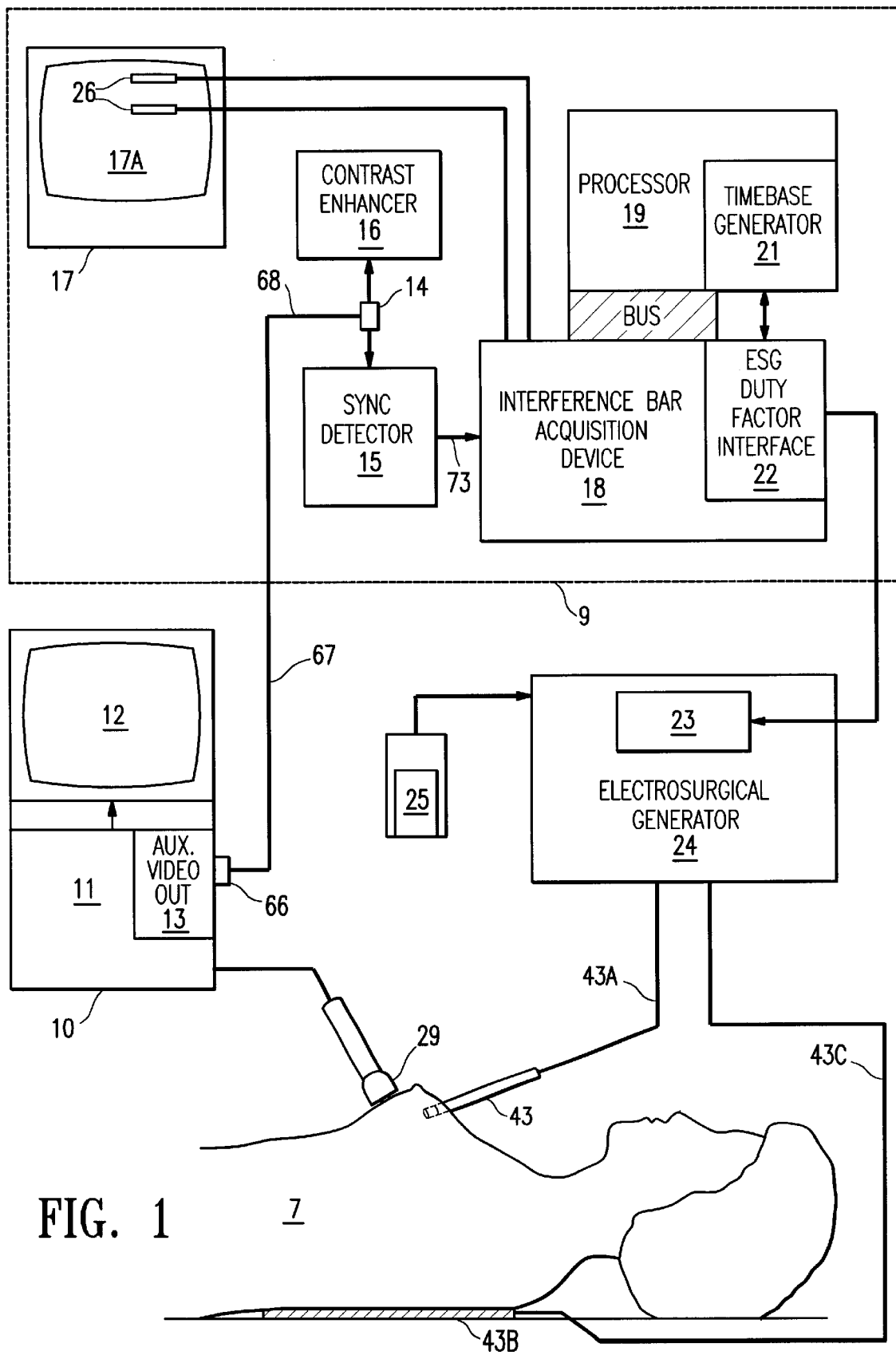
FIG. 1 shows a side elevational view of a patient and a schematic block diagram of an ultrasonic imaging, an electrosurgical instrument, and an interference reduction system having features of the invention.

FIG. 1 shows a side elevational view of a patient 7 and a schematic block diagram of an interference reduction system 9 which can be used with existing commercially available ultrasonic imaging systems 10.

Ultrasonic imaging system 10 has an ultrasound unit 11 and an ultrasound system video monitor 12. The ultrasound unit 11 is coupled by an auxiliary output port 13 to a signal splitter 14 of the interference reduction system 9. The signal splitter 14 is in turn coupled to both a sync detector 15 and a contrast enhancer 16. The contrast enhancer 16 is in turn coupled to a secondary video monitor 17 having a screen 17A. The sync detector 15 is coupled to an interference bar acquisition device 18 which is in turn bussed to a processor 19.

The processor 19 houses a timebase generator 21 which communicates with an electrosurgical duty factor interface 22. The duty factor interface 22 is in communication with an internal inhibitor 23 disposed within the electrosurgical generator 24. A footswitch 25 which enables the ESG 24 is also in communication with the ESG 24. Sensor boards 26 are disposed on the screen 17A of the secondary video monitor 17 and coupled to the interference bar acquisition device 18. The ESG 24 can be any of a variety of standard electrosurgical units generating radiofrequency energy in a range of about 350 to about 6,000 KHz, specifically, about 2,000 to about 5,000 KHz. Power output for the ESG 24 can be about 25 to about 1000 watts, preferably about 75 to about 300 watts.

In order to define the elements and function of the invention, some of the elements of a typical ultrasonic imaging system and the functions of those elements will be discussed hereafter in a simplified format. The interference problem caused by the operation of an energy emitting device, such as electro surgical generator, in conjunction with an ultrasonic imaging system will also be discussed.

Figure 2:
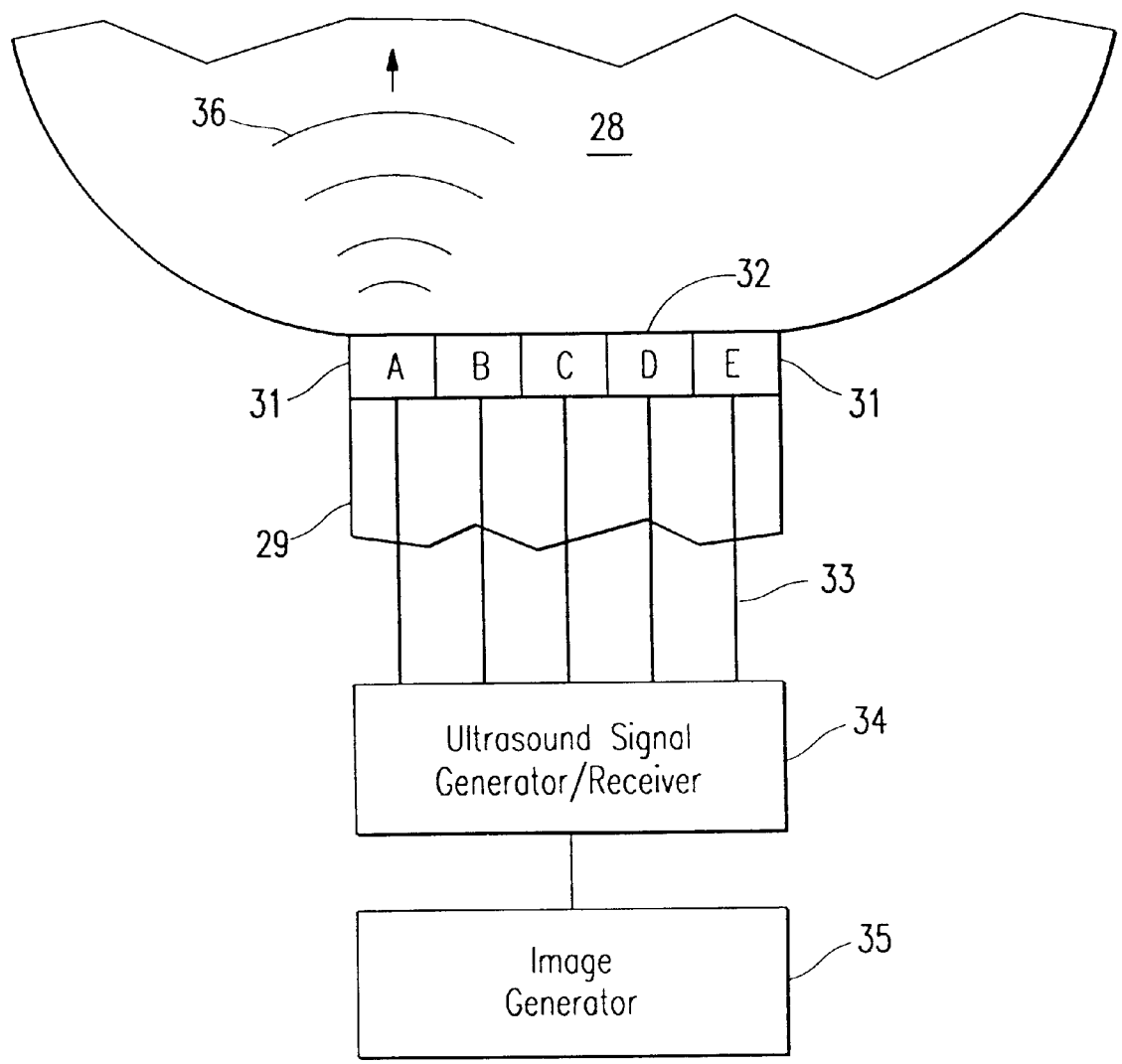
FIG. 2 is a side elevational view of tissue being imaged and a schematic block diagram of an ultrasonic transducer having five piezoelectric elements in a linear array against tissue being imaged, with the transducer elements coupled to an ultrasound image signal generator/receiver which is coupled to an image generator.

FIG. 2 is a side elevational view of tissue 28 being imaged by an ultrasonic transducer 29 having five piezoelectric elements 29 A–E disposed in a linear array. The piezo elements 31 lie against the tissue 28 being imaged and a liquid or gel may be used between the piezo elements and the tissue in order to facilitate transmission of ultrasound energy through the transducer/tissue interface 32.

The transducer elements 31 are coupled by a bipolar cable 33 to an ultrasound image signal generator/receiver 34 which is then coupled to an image generator 35. In operation, an ultrasonic imaging cycle is initiated by the ultrasound signal generator 34 sending a pulse of electrical energy at ultrasonic frequency to piezo transducer 29 element A. Transducer element A then emits ultrasonic energy 36 into the tissue 28 of interest as shown.

Note that portions of the reflected ultrasonic energy 37 also impinge on other adjacent piezo transducer elements 31 and produces electrical signals in those elements 31 as well. Depending on the specific ultrasound system 10 being used, these additional signals may or may not be used to generate an image. It should also be noted that although the transducer shown in FIGS. 2 and 3 has only five piezo elements 31 in a linear array, the piezo elements 31 could be arranged in a non-linear array and the number of elements in most commercially available ultrasonic imaging systems is typically much greater than five. A commonly used ultrasound imaging system 10 is the General Electric® System Model Logiq-400. This ultrasound system 10 uses 128 elements in a linear array. The invention is, however, adaptable to a wide variety of imaging systems as discussed above, including ultrasonic imaging systems using any number of piezo elements. 31 FIGS. 2 and 3 show five piezo elements 31 for the purpose of clarity of illustration only.

Figure 3:
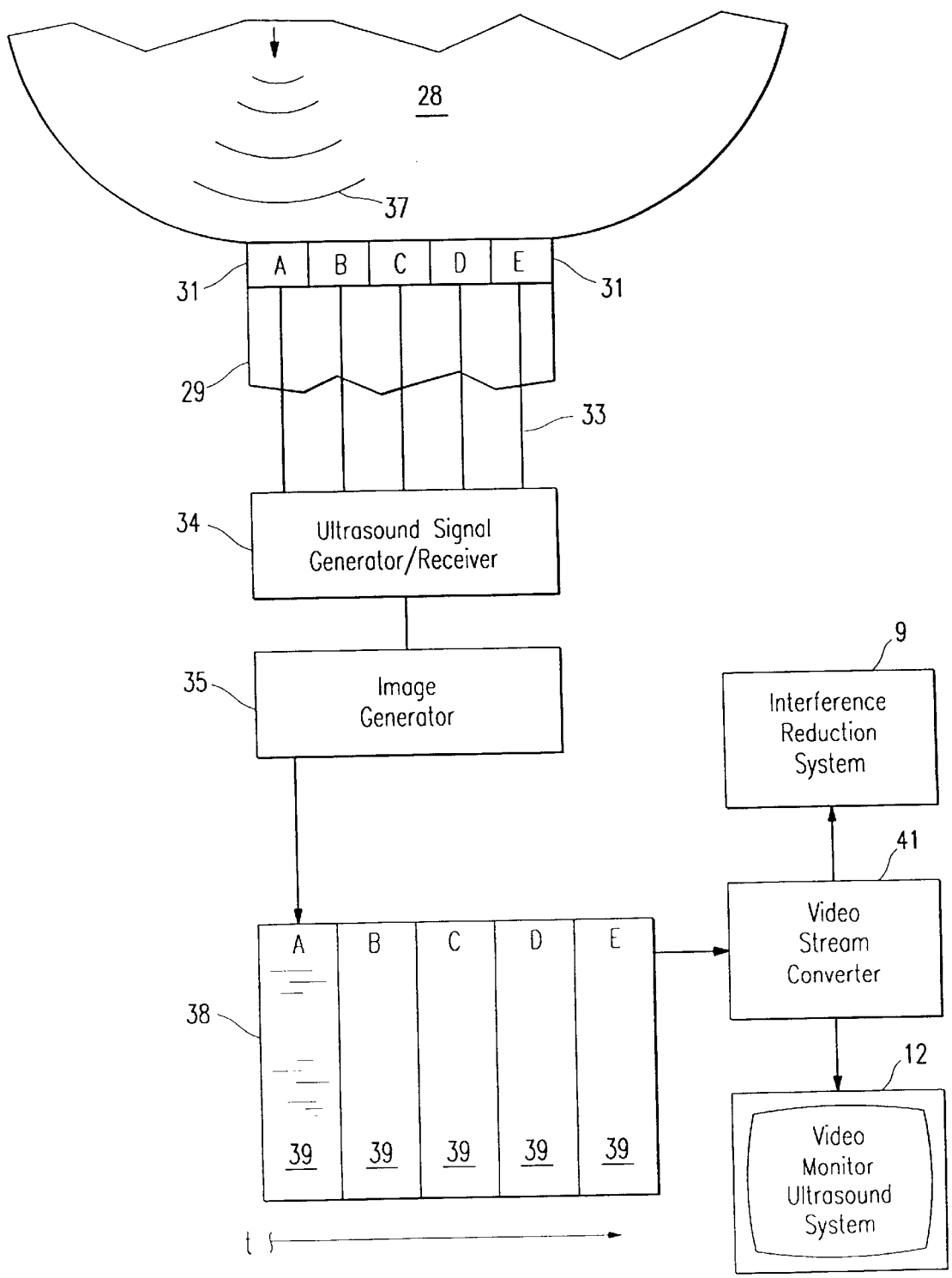
FIG. 3 is a side elevational view of tissue being imaged and a schematic block diagram of the tissue and device of FIG. 2, further showing an image frame with vertical columns corresponding to elements A–E coupled to a video stream converter which is coupled to an interference reduction system and a video monitor.

As shown in FIG. 3, the ultrasonic energy 37 is reflected by various portions of the tissue 28 of interest and impinges back onto transducer element A and generates an electric signal. The electrical signal generated by element A then travels to the ultrasound signal generator/receiver 34 which has been switched to receiver mode. The signal is then amplified and forwarded to an image generator 35 which further processes the image signal and begins creation of an image frame 38 which is constructed with one column 39 corresponding to each piezo element 31 A–E. Thus, the reflected ultrasonic image data collected from the signal transmitted by element A will be processed and stored to corresponding column A of the image frame 38. The image frame 38 is an internally stored image that is not immediately visible on the external video display monitor 12.

Figure 4:
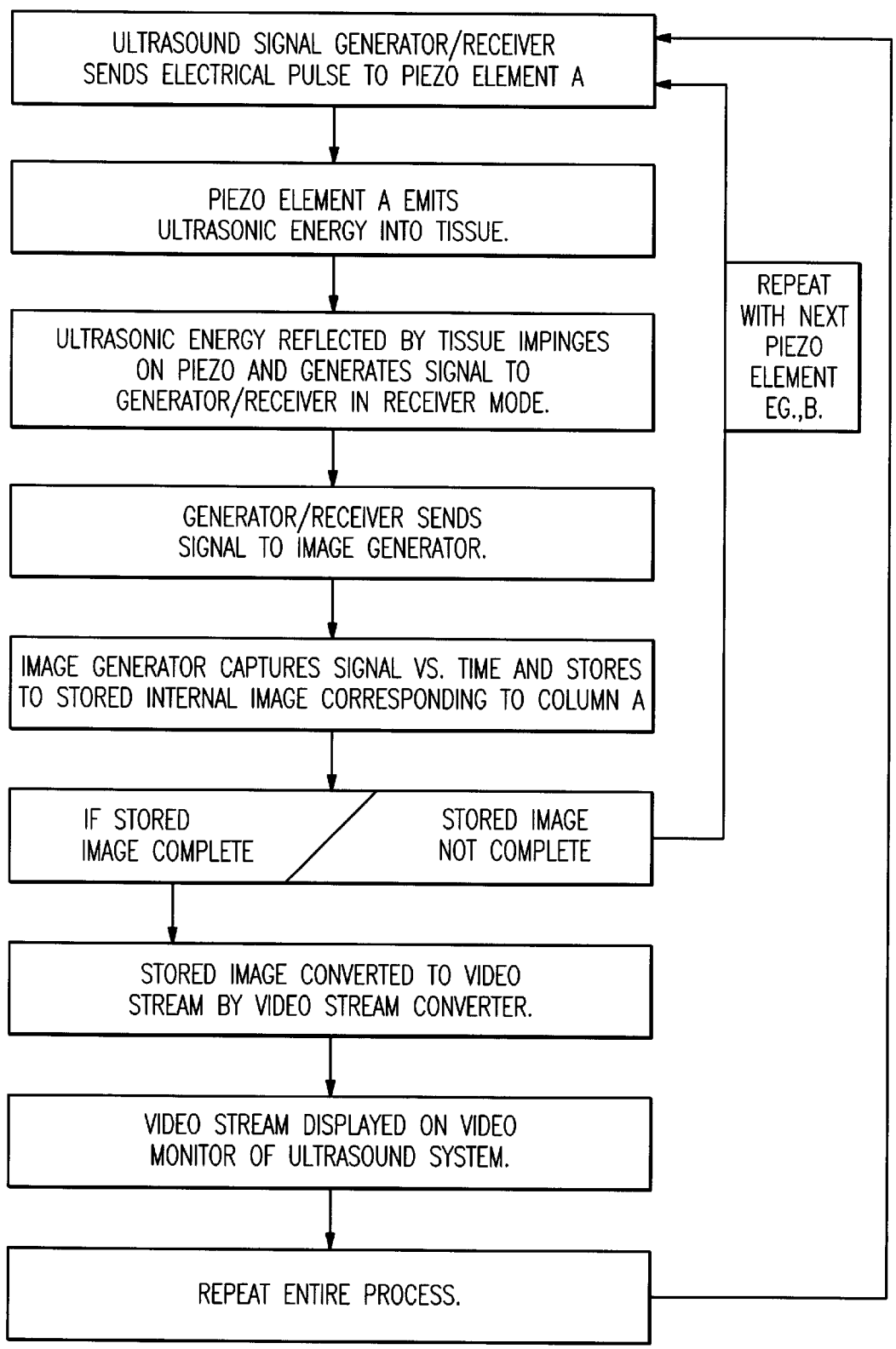
FIG. 4 is a flowchart depicting some of the operational steps performed in an ultrasonic imaging system in a simplified format.

Once all useful reflected ultrasonic energy 37 from element A has been received, piezo element B is activated with an electrical signal and the process repeats. In this way, the image frame 38 is constructed one column 39 at a time with each column 39 corresponding to an individual or set of individual piezo elements 31. When all columns 39 A–E of the image frame 38 have been constructed, the stored image frame data is forwarded to a video stream converter 41 which then displays the image frame 38 as video stream data on the video monitor 12. The video stream data is raster scanned as a video image frame onto the screen lines of the video monitor 12 at a rate of approximately one full screen image every 1/30th of a second. Although the raster scan process occurs at a rate of 60 Hz, only odd or even lines of the monitor screen are scanned for each raster scan cycle. Thus, the screen must be scanned twice at 60 Hz in order to produce a complete video image frame, thereby requiring 1/30th of a second. The raster scan process can be controlled by a video sync signal which determines where one video image frame ends and the next begins. A flowchart 42 of the above described simplified sequence for ultrasonic imaging is shown in FIG. 4.

It should also be noted that the raster scan rates discussed above apply generally to NTSC video system formats. Other video system formats, such as PAL, can be similar but PAL operates at approximately 50 Hz for example. In addition, still other video formats can be used such as those compatible with personal computer system format displays, e.g., VGA, SVGA and the like. In these systems, the video sync signal may not have to separated from the video stream signal by a distinct operation of the invention.

The piezo elements 31 and corresponding circuitry are generally most susceptible to electrical and electromagnetic interference when the signal generator/receiver 34 is in receive mode. As such, if an energy emitting instrument such as the electrosurgical probe 43, in contact with a patient 7 or other mass being imaged is operated while the ultrasound imaging system 10 is operating, energy from the energy emitting instrument 43 can impinge on the transducer 29 and interfere with or saturate the image frame 38 corresponding to the time period during which operation of the instrument 43 occurred.

The primary path of travel of radio frequency energy emitted from monopolar electrosurgical probe 43 begins at ESG 24 where the radiofrequency energy is first generated or synthesized. The radio frequency energy then travels through a first ESG conduit 43A to electrosurgical probe 43. The energy is then emitted from the probe 43 into the patient 7 where the desired ablation, cutting or coagulation of tissue takes place. The radiofrequency energy then travels to ground plate 43B and returns to ESG 24 via a second ESG conduit 43C which completes the circuit. Although the above described circuit is the primary path of travel of radiofrequency energy, portions of the radiofrequency energy stray from the electro surgical probe 43 to ground sites within the patient other than the tissue adjacent ground plate 43B. The same holds for bipolar electrosurgical probes wherein the electrical equivalent of ground plate 43B consists of a return electrode disposed somewhere on the electro surgical probe 43.

Figure 5:
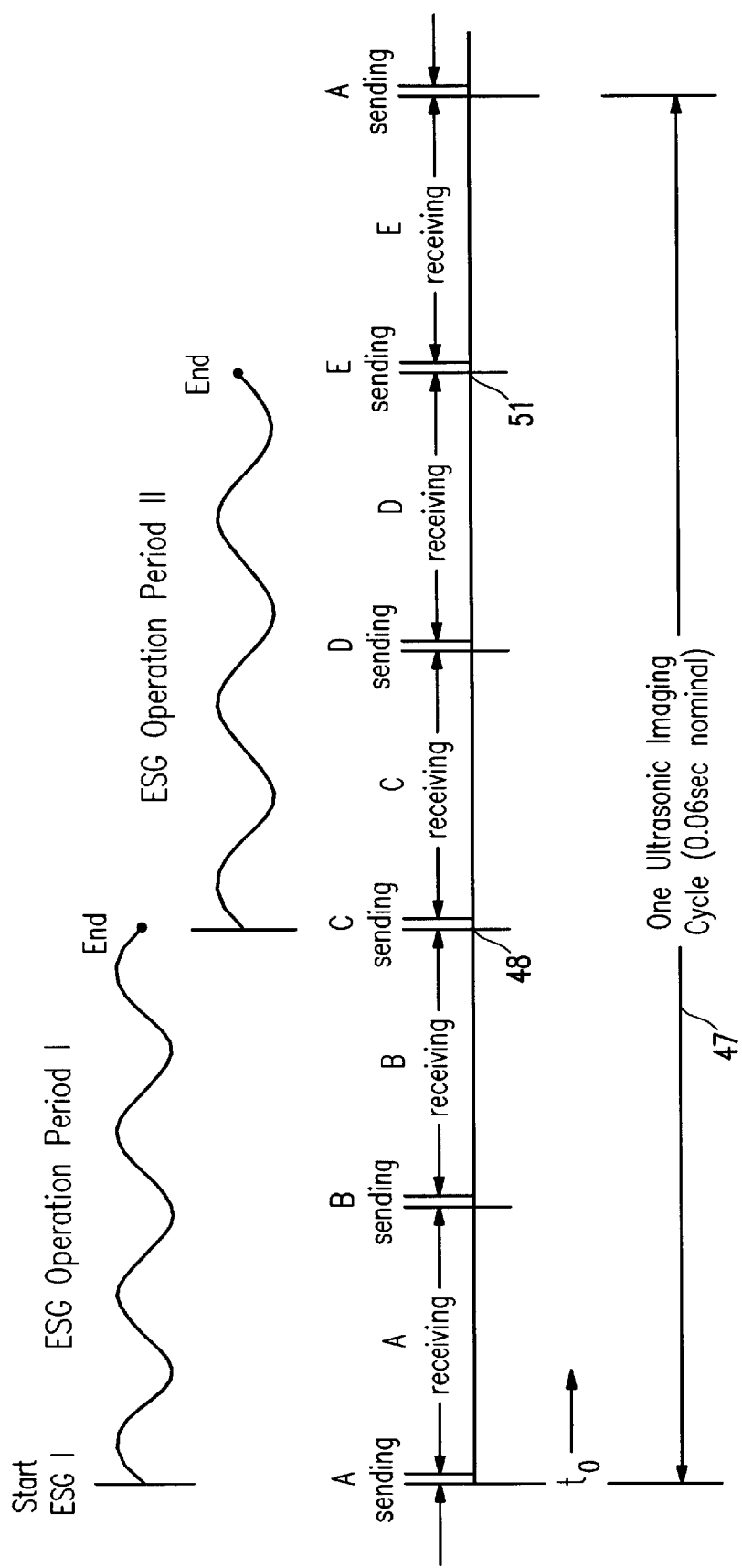
FIG. 5 is a graphical view illustrating the chronological relationship between the sending and receiving phases of individual transducer elements and a first period of ESG operation I. and a second period of ESG operation II. in the context of one ultrasonic imaging cycle.
Figure 6:
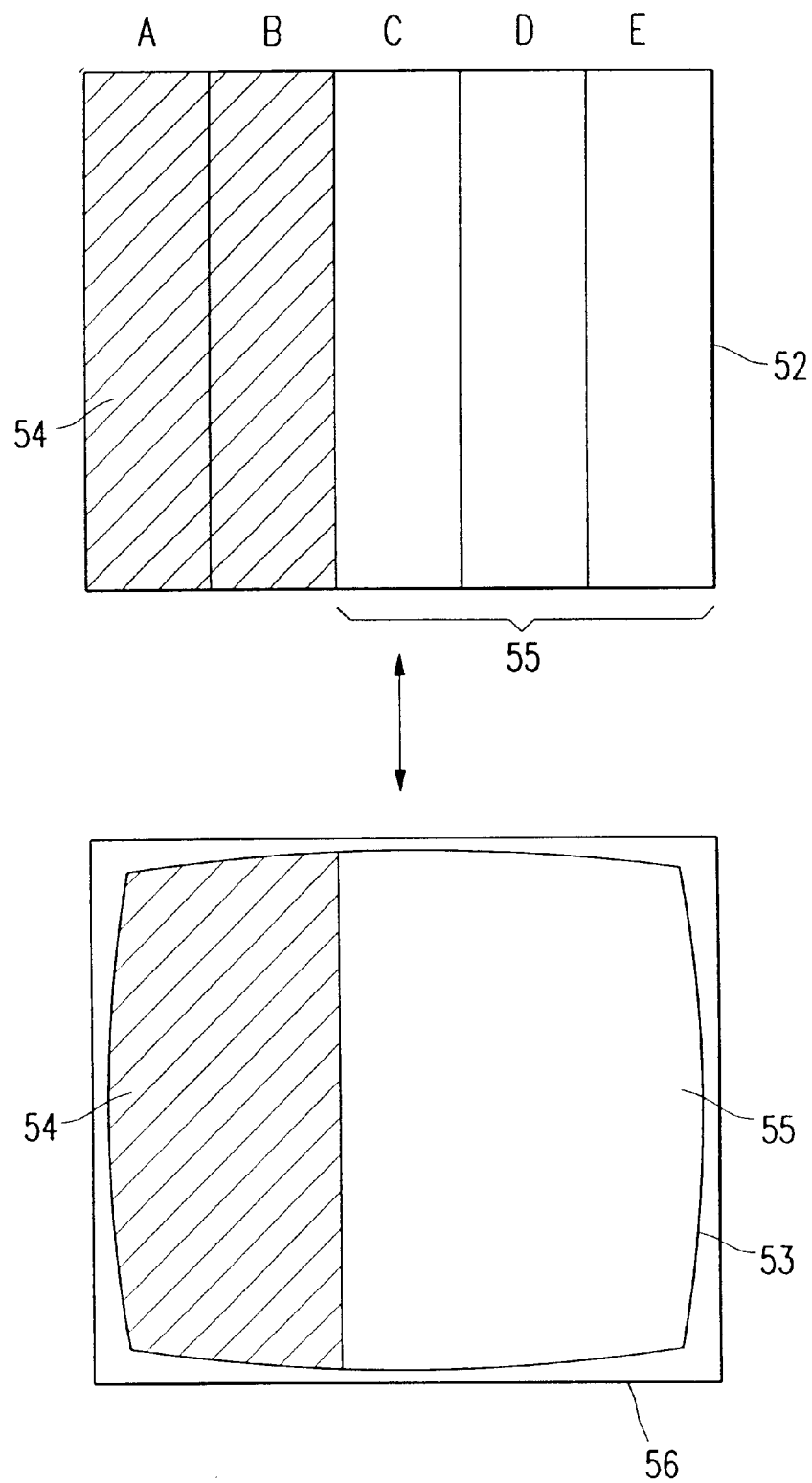
FIG. 6 is block diagram showing an image frame with interference in the two left image frame columns A and B, and the corresponding display image on a video monitor.
Figure 7:
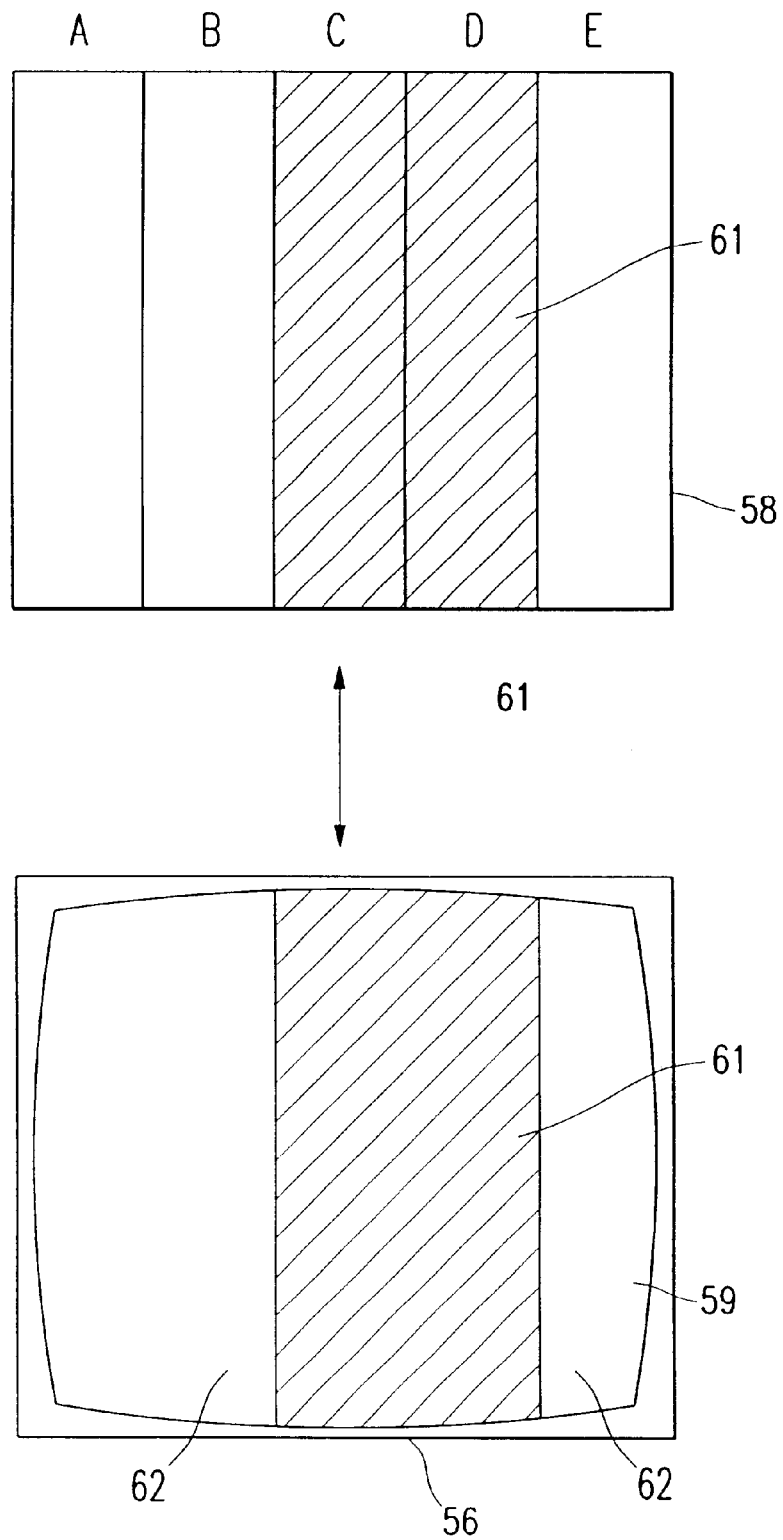
FIG. 7 is block diagram showing an image frame with interference in image frame columns C and D, and the corresponding display image on a video monitor.

FIGS. 5–7 graphically illustrate the chronological relationship between the sending and receiving phases of individual transducer elements 31 and a first period of ESG operation I. and a second period of ESG operation II. in the context of one ultrasonic imaging cycle 47. As seen in FIG. 5, element A begins emission of ultrasonic energy into target tissue 28 at time $t_0$. ESG operation period I. begins at the same time. ESG operation period I. ends at the end of the receiving period of element B, indicated by reference numeral 48, at which time ESG operation period II. begins. ESG operation period II. ends at the end of the receiving period of element D, indicated by reference numeral 51. There is no ESG operation during the sending or receiving periods of element E.

FIG. 6 illustrates an image frame 52 and corresponding video image frame display 53 of the interference bar 54 that would be produced in a given image frame resulting from a single ultrasonic imaging cycle in which only ESG operation period I. occurred. As seen in the image frame 52 of FIG. 6, both columns A and B have been completely obscured and saturated by interference bar 54 from operation of the ESG during period I. corresponding to columns A and B. The unperturbed image 55 shown in columns C, D and E of FIG. 6 is not affected by the ESG operation period I. and a corresponding video frame image 53 free of interference bar 54 is shown on the display monitor 56. As is apparent from this illustration, the width of the interference bar 54 produced by operation of the ESG 24 during the ultrasonic imaging cycle is proportional to the duration of the period of operation of the ESG 24.

Although FIG. 6 shows interference bar 54 as a rectangular bar with clean well defined edges, the term "interference bar" as used herein can encompass any pattern of interference generated within any type of imaging system. For example, interference bar 54 may be in the form of a wedge or parallelogram with slanted or carved leading or trailing edges.

It should be noted that the top of column A in the stored image frame 52 of FIG. 6 corresponds to the left side of the receiving period for element A in FIG. 5 and the bottom of column A in the stored image frame 52 corresponds to the right side of the receiving period for element A in FIG. 5. In other words, column A in the image frame is built over time, starting at the top and building down as reflected imaging signals are detected over time at element A. The same holds true for the remaining elements B–E and the corresponding image frame columns in FIG. 6. With regard to the period of the ultrasonic imaging cycle, it can vary significantly depending on the particular ultrasound imaging system 10, and the operator's selection of variable imaging parameters on that system 10.

The imaging depth set by the operator can affect the period for the ultrasound imaging cycle. This is because the deeper the operator wishes to image, the longer it will take for the emitted ultrasound signal from each piezo element 31 to be reflected and return to the piezo element 31 to generate an imaging signal due to the increased path of travel of the signal. For a typical ultrasound imaging system 10 such as the General Electric® system described above, and for typical imaging settings which are controllable by the operator, the frequency of the ultrasonic imaging cycles can be about 5 to about 50 Hz, specifically, about 10 to about 30 Hz and more specifically about 15 to about 25 Hz. This can produce a nominal ultrasonic imaging cycle period of about 0.05 to about 0.07 seconds, or about 0.06 seconds for the ultrasound imaging cycle.

FIG. 7 illustrates an image frame 58 and corresponding video image frame display 59 of the interference bar 61 that would be produced in a given image frame 58 resulting from a single ultrasonic imaging cycle in which only ESG 24 operation period II. occurred. As seen in the image frame 58 of FIG. 7, both columns C and D have been completely obscured and saturated by interference bar 61 from operation of the ESG 24 during period II. corresponding to columns C and D. The unperturbed portion of the image 62 shown in columns A, B and E of FIG. 7 were not affected by the ESG 24 operation period II. and a corresponding video image frame 59 free of interference is shown on the display monitor 56. If the image frame 52 of FIG. 6 and the image frame 58 of FIG. 7 were consecutive image frames, the interference bars 54 and 61 would appear to be travelling from left to right across the screen. Such an effect is produced when the ESG 24 is operated at an interruption frequency near that of the ultrasound imaging cycle.

The present invention is configured to detect the existence of an interference bar 54 and 61 such as illustrated in FIGS. 6 and 7 and adjust the frequency and phase of the ESG 24 operation in relation to the frequency and phase of the ultrasonic imaging cycle in order to fix the position of the interference bar 54 and 61 caused by operation of the ESG 24 during the ultrasonic imaging cycle so that it does not move across the screen and obscure the operator's view. More specifically, it is desirable to fix the position of the interference bar 54 and 61 in a location at a perimeter or perimeters of an affected image frame 52 and 58 and corresponding video display image 53 and 59 so that the interference bar 54 and 61 is at the borders of the displayed image and does not interfere with the operator's view of the center of the image.

Figure 8:
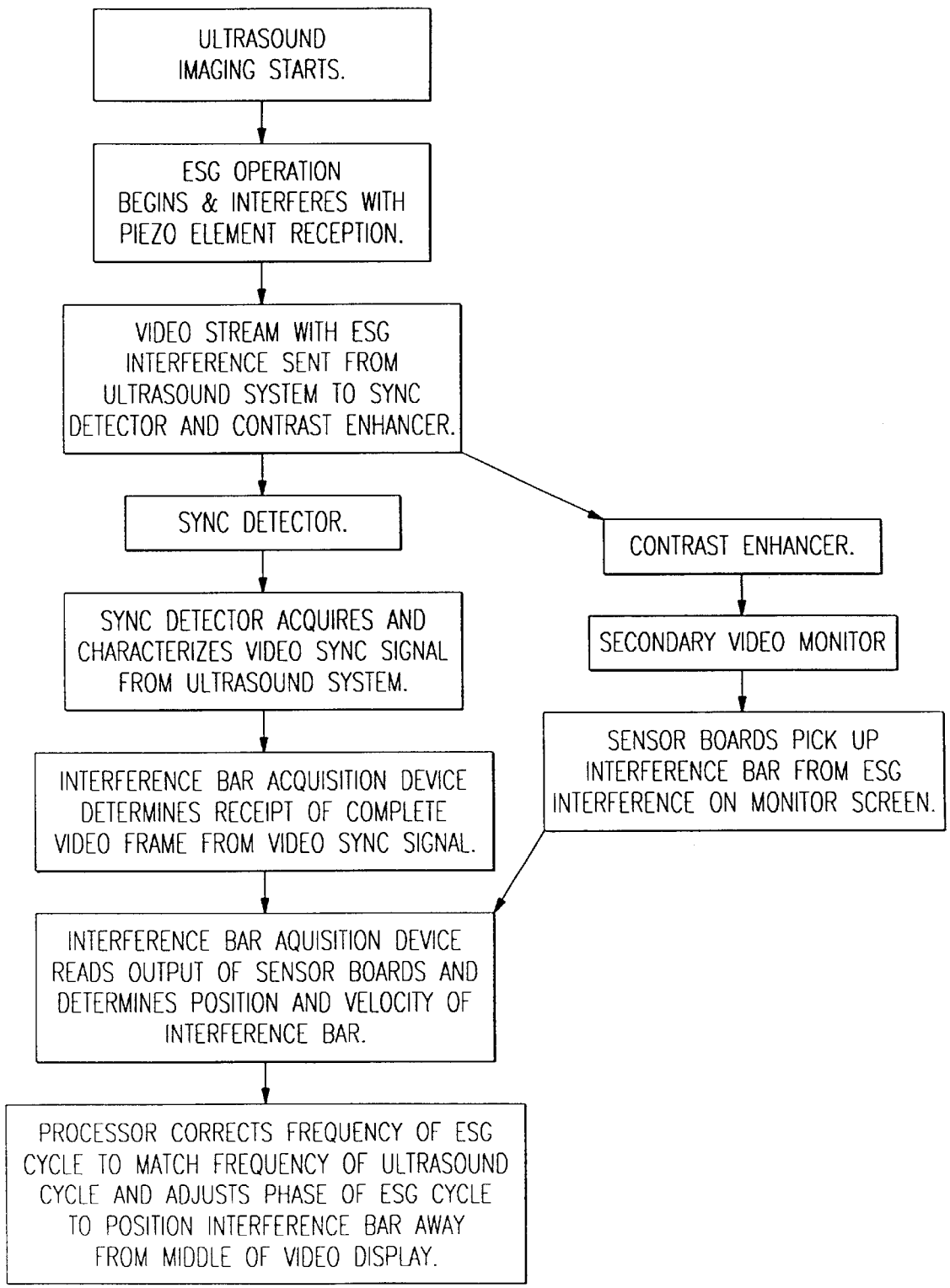
FIG. 8 is a flowchart of some of the processes of an embodiment of the invention shown in FIG. 1 for adjusting the frequency and phase of the intermittent operation of an electrosurgical generator in order to fix the position of an interference bar in a desired location within an image frame.

FIG. 8 is a flowchart of a process of an embodiment of the invention shown in FIG. 1 for adjusting the frequency and/or phase of the intermittent operation of an electrosurgical generator 24 in order to fix the position of an interference bar 54 and 61 created thereby in a desired location within an image frame 52 and 58.

Referring again to FIG. 1, the ultrasonic imaging system 10 has an ultrasound unit 11 and an ultrasonic system video monitor 12. The ultrasound unit 11 has an auxiliary video out port 13 which transmits a duplicate video signal to that sent to the ultrasound system video monitor 12. A standard bnc connector 66 and coaxial cable 67 is secured to the auxiliary video out port 13 at a first end of the coaxial cable 67. A second end 68 of the coaxial cable 67 is coupled to a signal splifter 14 which is then coupled to a sync detector 15 and an optional contrast enhancer 16.

The sync detector 15 is also coupled with a cable 73 to an interference bar acquisition device 18. In one embodiment, the sync detector 15 and interference bar acquisition device 18 are on the same printed circuit board (PCB), thereby eliminating the need for cable 73. A video stream signal sent from the ultrasound unit 11 to the auxiliary video out port 13 then travels to the signal splitter 14 and into the sync detector 15. The sync detector 15 processes the video signal and captures the video sync signal and relays the sync signal data to the interference bar acquisition device 18. The interference bar acquisition device 18 is coupled to a processor 19 which uses the sync signal data generated by the sync detector 15 and interference bar acquisition device 18 to determine when a complete video image frame has been sent by the ultrasound unit 11 to the video display 12 and secondary video monitor 17.

Once a complete video frame has been transmitted by the ultrasound unit 11 to the secondary video monitor 17, interference bar position data generated by sensor boards 26 for that complete video image frame which was sent and stored to the interference bar acquisition device 18, can then be read and analyzed by the processor 19. Thus, the processor 19 is generally configured to read sensor board 26 data only after a complete video image frame is received in order to avoid erroneous data that might be derived from a partial video image frame.

In parallel to the sync signal capture process just discussed, the same video stream data that was diverted by the signal splitter 14 to sync detector 15 also gets split off by the signal splitter 14 to the contrast enhancer 16. The contrast enhancer 16 processes the video stream data and enhances the contrast of the electronic image by raising the brightness of any pixel of video stream data which is over a predetermined threshold value of brightness. In this way, the boundaries of an interference bar 54 and 61 embedded in the video stream data will be more reliably read and discriminated by the photo diodes 79 of the sensor boards 26. Once the video stream signal has been enhanced by the contrast enhancer 16, the signal is sent to a secondary video monitor 17 which displays the video image frames of the video stream signal on screen 17A.

Figure 14:
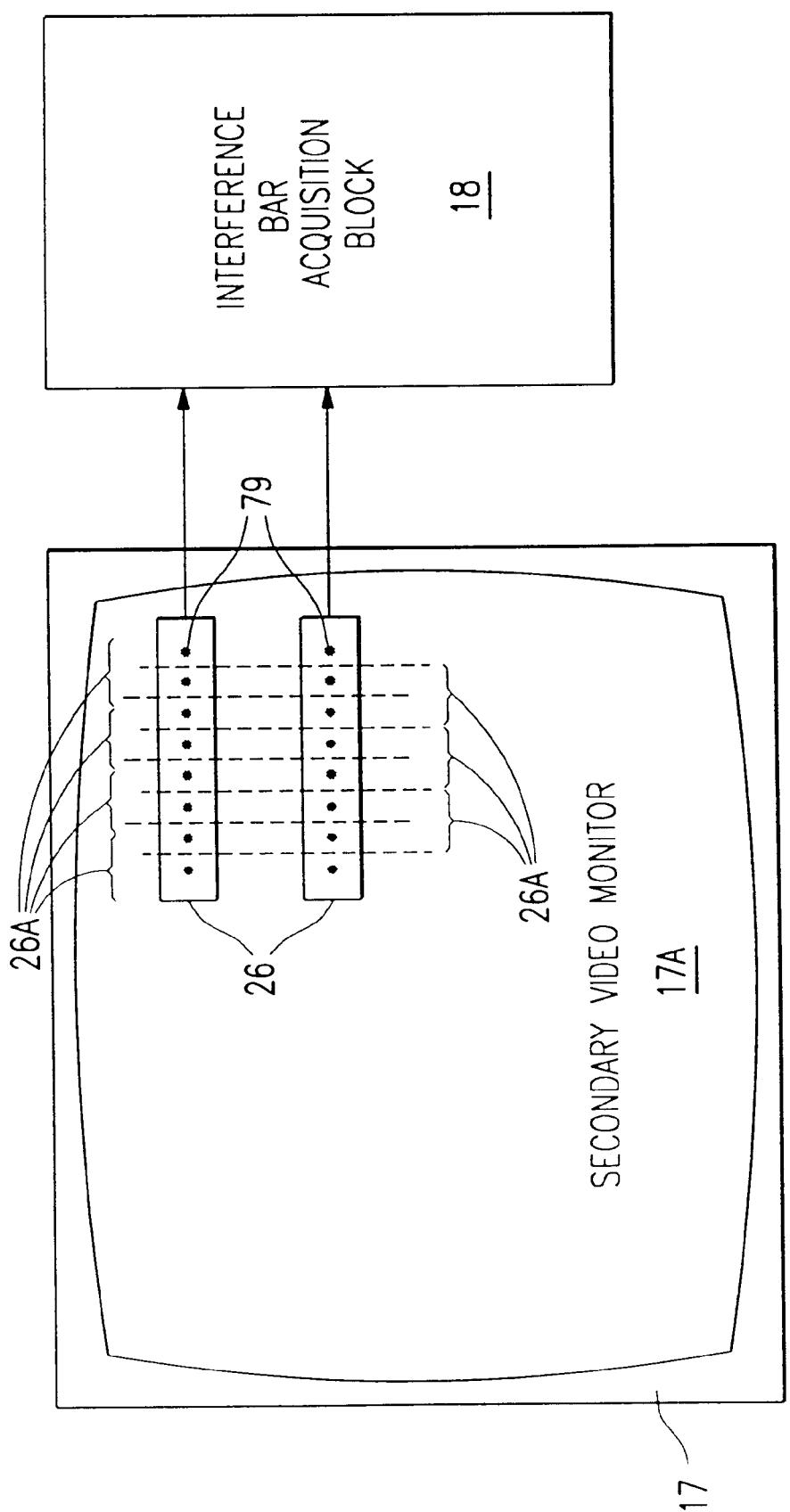
FIG. 14 is an elevational view of a secondary video monitor with sensor boards disposed on the screen thereof and a block diagram view of a bar acquisition processor in communication with the sensor boards.
Figure 15:
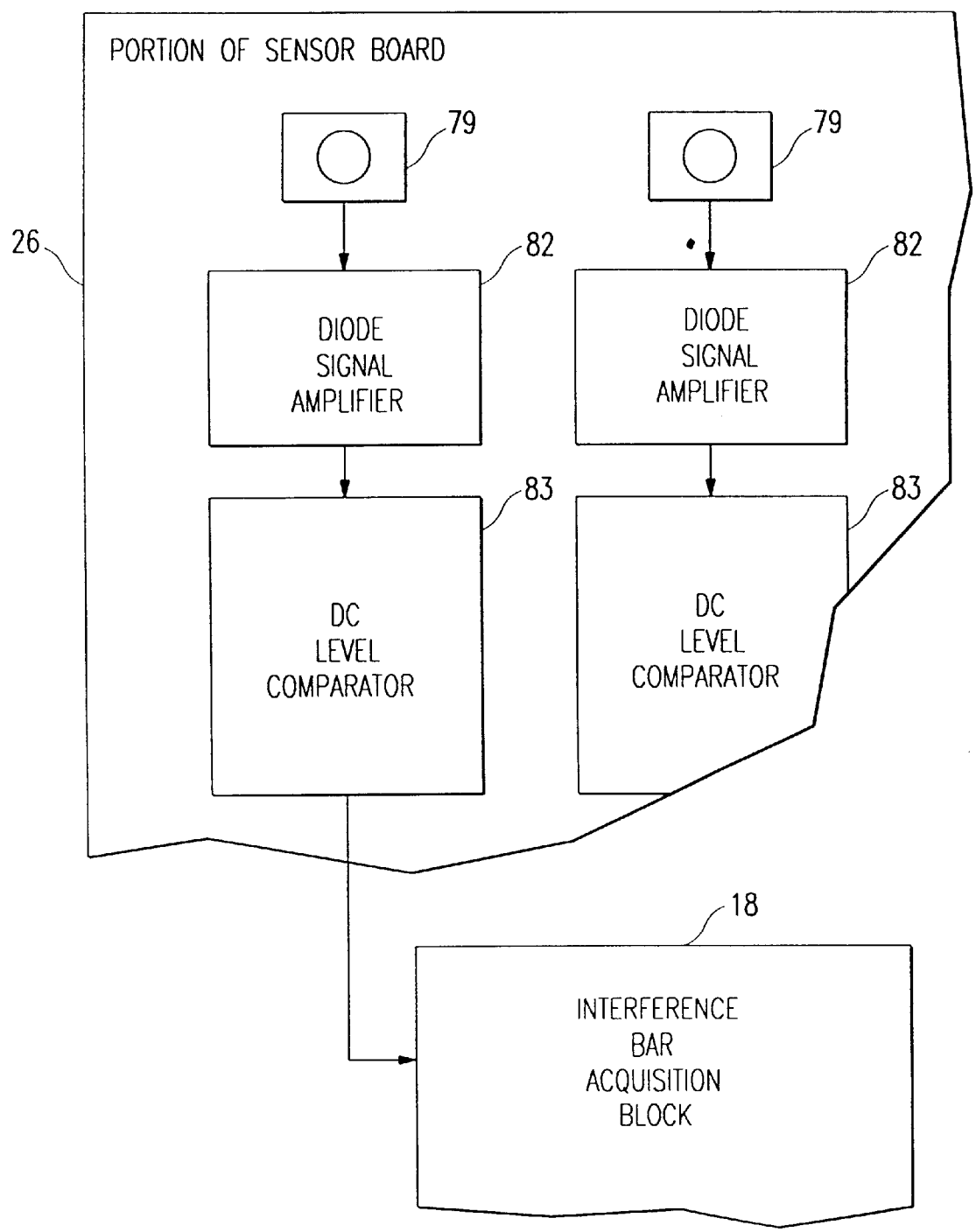
FIG. 15 is an enlarged view partially broken away of one of the sensor boards shown in FIG. 14.

An interference bar 54 and 61 which is embedded in the enhanced video stream signal will then be displayed on the screen 17A of the secondary video monitor 17 and sensed by the sensor boards 26. Referring to FIGS. 14 and 15, the sensor boards 26 will send digital data generated from the analog output of each of the photo diodes 79 on the sensor boards 26 to the interference bar acquisition block 18. Each diode 79 has a separate amplifier 82 and DC level comparator 83 that determine whether the image on screen 17A beneath the diode 79 displays a bright enough signal to constitute a portion of an interference bar 54 and 61.

Various logic sequences can be used to poll the information obtained by the diodes 79 of the sensor board 26 during a video image frame cycle to determine if an interference bar 54 and 61 is present. In one embodiment, each sensor board 26 has 8 diodes 79 linearly distributed therein at regularly spaced intervals There are two such sensor boards 26 disposed on the screen 17A of the secondary monitor 17 with the linear array of the photodiodes 79 of each sensor board 26 oriented horizontally. The sensor boards 26 are vertically aligned so that vertical line of interference, i.e., an interference bar, moving laterally across the screen 17A of the secondary video monitor 17 will be detected by corresponding diodes 79 from each of the sensor boards 26. As discussed above, although the interference bars illustrated herein are in the form of rectangular bars of interference, the term "interference bar" is intended to encompass any pattern of interference which partially obscures the display of an imaging system. An interference bar may be in the form of a wedge, parallelogram or the like such that the leading or trailing edges of the interference bar are not vertical lines as discussed immediately above. The signal generated by each diode 79 disposed on the sensor boards is amplified via a transimpedance amplifier 82, then digitized by processing through a DC level comparator 83. The 8 resulting bits of data for each sensor board 26 are then processed to determine if the image being detected by the diodes 79 is a continuous feature, such as an interference bar, or noise.

The detection of an interference bar in one embodiment is achieved by a voting system. The sixteen diodes 79 of the two sensor boards 26 are divided into seven sensor board diode zones, shown as sensor board diode zones 26A as separated and defined by the broken lines shown in FIG. 14. Thus, the seven sensor board diode zones having four diodes 79 in each, actually overlap by one column of diodes 79. Each sensor board diode zone 26A consists of a 2×2 matrix of diodes 79 for a total of four diodes 79 per zone.

It can be desirable for the sensor board diode zones 26A to consist of at least some diodes 79 from each of the two sensor boards 26 as the vertical alignment and separation of the two sensor boards 26 can help to eliminate false positive readings. Using vertically aligned diodes 79 from each sensor board 26 for any given sensor board diode zone 26A allows for improved detection and distinction of vertical lines of interference such as that created by an interference bar. In other words, an interference bar having well defined and vertically oriented lateral boundaries, such as interference bar 54, should give positive readings on the diodes 79 of both sensor boards 26 within a sensor board diode zone 26A which covers such an interference bar 54 during a video image cycle.

To determine if an interference bar is being detected by the diodes 79 of a given sensor board diode zone 26A, as opposed to detection of random interference or a portion of a sonogram image, the following voting system can be used by processor 19. If any three of the four sensors of a sensor board diode zone detect a positive signal, i.e., a signal above a predetermined threshold value, for any given video image frame, one bit of a bit map representing the linear position of an interference bar is set. This method results in a useable seven bits of information regarding a sensed interference bar for each video image frame. It may also be necessary to further process the seven bits of data from the sensor board interference zones 26A to provide added resolution of an interference bar 54 that has poorly defined lateral edges or is otherwise poorly defined and inconsistent.

The processor 19 can read the resolved seven bit field at the end of each ultrasound imaging cycle. Because the nominal ultrasonic imaging cycle is operating at about 15 to about 25 Hz, and the video image frame is being refreshed at a nominal rate of about 30 Hz, two or more of the same video image frames may be raster scanned onto the screen of the secondary monitor 17 for each ultrasonic imaging cycle. By evaluating the bit pattern, the processor 19 can determine where on the sensor board 26 the interference bar 54 is positioned within the ultrasound image frame and corresponding video image frame. The processor 19 then stores the location data for the measured interference bar 54.

The position data is then used to calculate the velocity of the interference bar by comparing the position of the interference bar in the first ultrasound image frame with the position of the interference bar in a subsequent ultrasound image frame. The velocity of the interference bar 54 corresponds to the magnitude and polarity of frequency and phase error of the ESG 24 timebase and corrections can then be made thereto by the processor 19 on an iterative basis. That is, the interference bar 54 position is detected for each ultrasound image frame. By looking at the position of the previously detected interference bar 54 and the position of a current interference bar 54, the processor 19 can calculate the velocity and direction of the interference bar 54 motion. This correlates to the frequency error between the ESG 24 interruption timebase frequency and the ultrasound imaging cycle frequency or frame rate, allowing a corrected frequency to be calculated by processor 19. The corrected frequency is communicated from the processor 19 to the ESG 24 via the timebase generator 21, ESG duty factor interface 22, and internal inhibitor 23. As discussed above, this is generally an iterative process, such that the error or difference between the frequency of the ultrasound imaging cycle and the ESG 24 interruption timebase frequency is reduced in consecutive image frames until the interference bar 54 is stable and positioned as desired.

Figure 9:
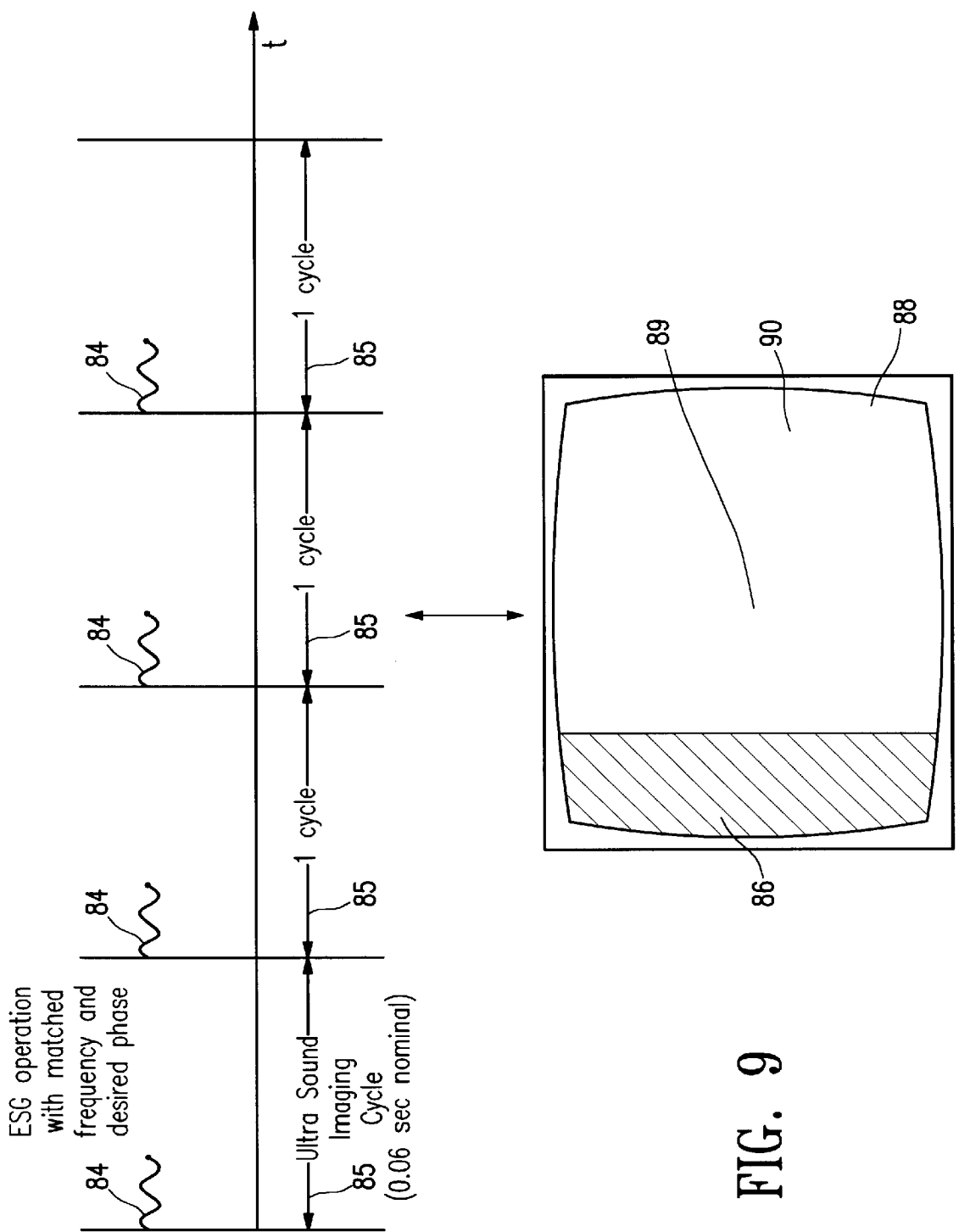
FIG. 9 is a graphical view of the chronology of intermittent ESG operation which has been synchronized with a frequency of an ultrasonic imaging cycle and phased to operate for only the first portion of each consecutive imaging cycle. Also shown is an elevational view of a corresponding video display of the interference resulting from such an ultrasonic imaging cycle and synchronized ESG operation.

FIG. 9 illustrates a graphical view of a chronology of intermittent ESG 24 operation 84 which has been synchronized with a frequency of an ultrasonic imaging cycle 85 and phased to operate for only the first portion of each consecutive ultrasonic imaging cycle 85 of multiple imaging cycles. The corresponding video display of the interference bar 86 resulting from such an ultrasonic imaging cycle 85 and synchronized ESG 24 operation sequence 84. Note that the interference portion 85 of the display on the video monitor 88 appears stationary and does not obscure an operator's view of the center 89 of the displayed image 90.

Figure 10:
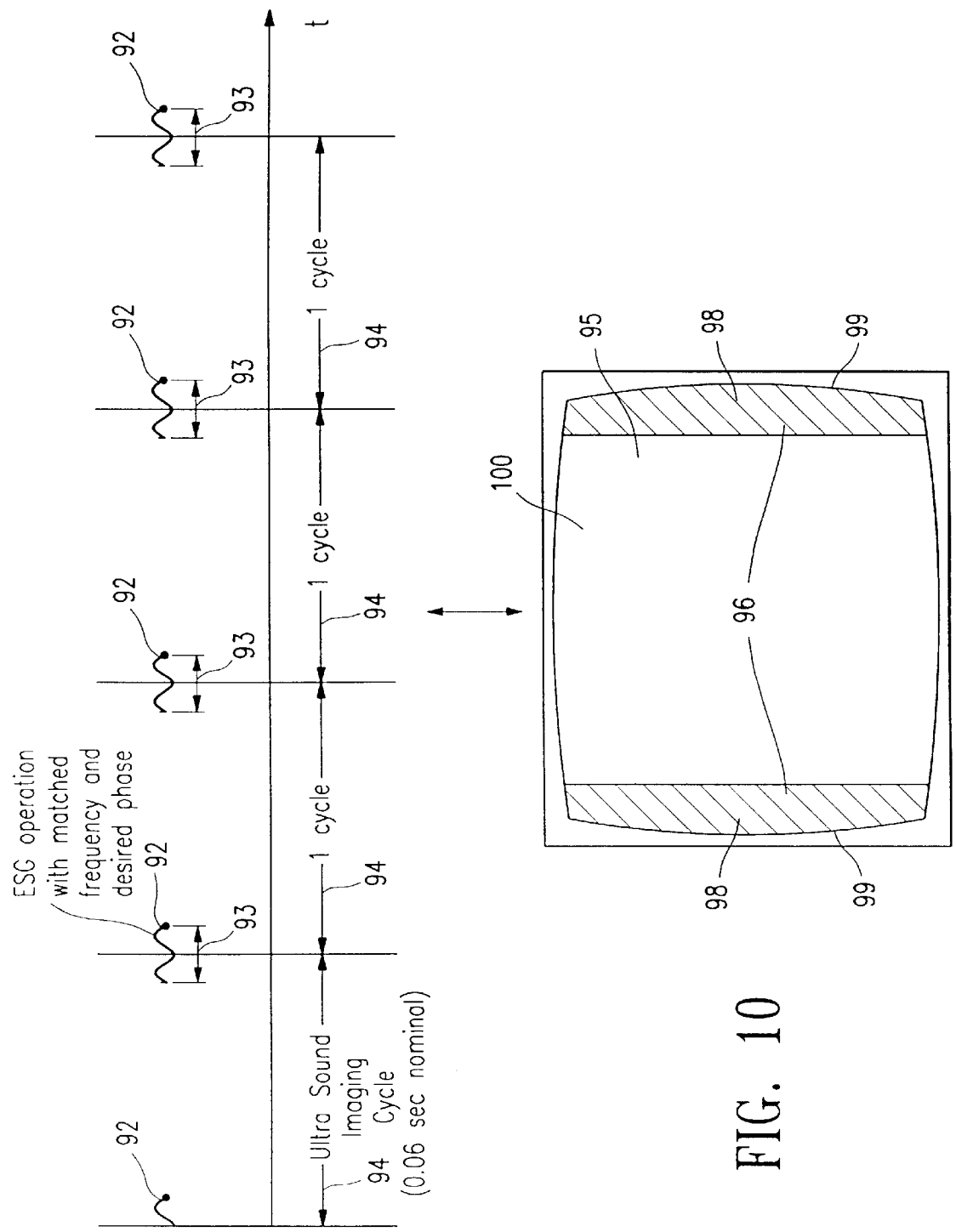
FIG. 10 is a graphical representation similar to FIG. 9 except that the ESG operation has been synchronized and phased to operate at intervals which overlap the end and beginning of consecutive imaging cycles. The corresponding video display is also shown.

FIG. 10 is a graphical representation similar to FIG. 9 except that the ESG operation 92 has been synchronized and phased to operate at intervals 93 which overlap the end and beginning of consecutive ultrasonic imaging cycles 94. The corresponding video image 95 is also shown. Here, the interference bar 96 has been effectively split and the display video image 95 portions having ESG interference 98 are at opposite lateral edges 99 of the display screen 100.

Figure 11:
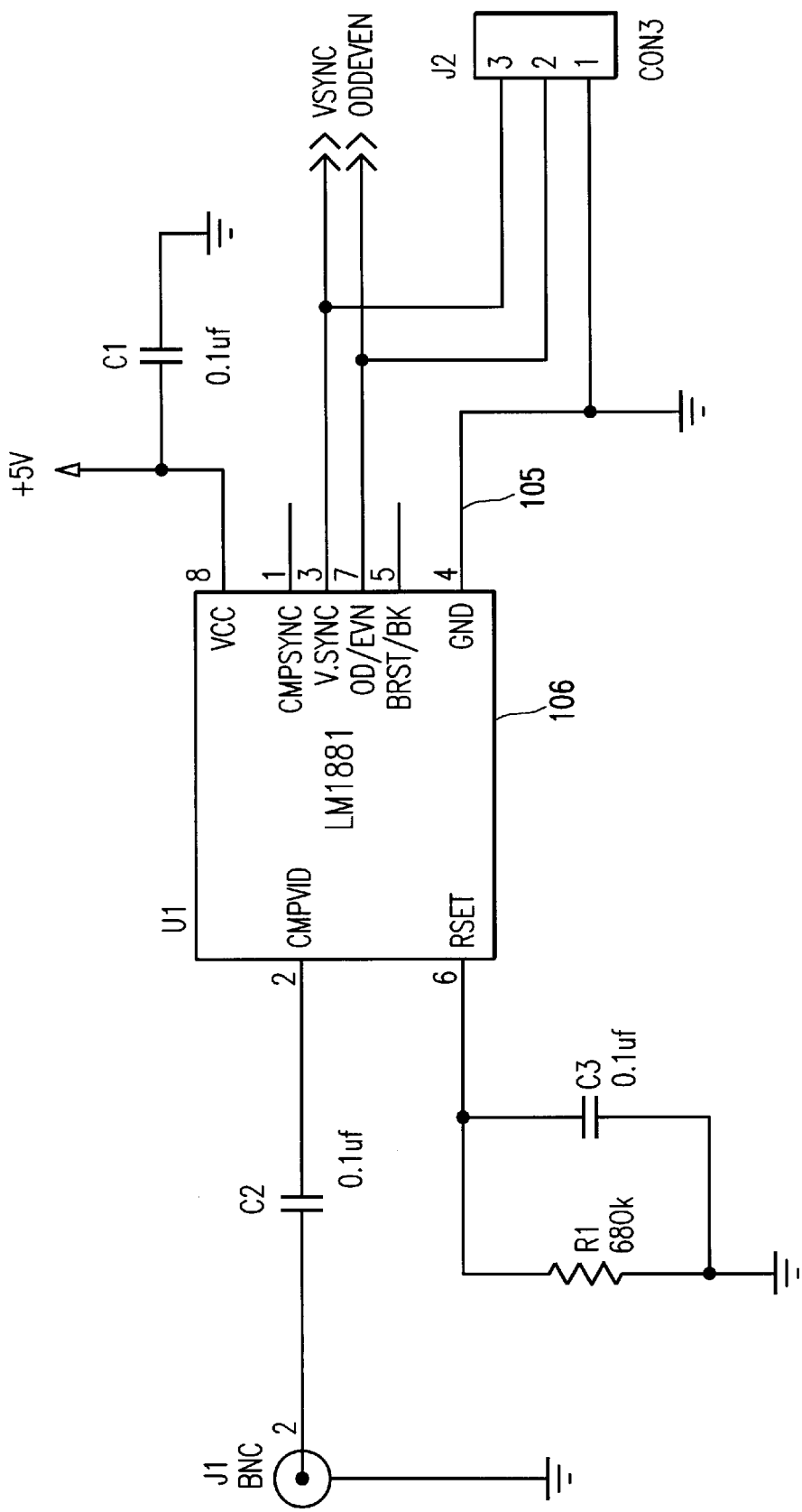
FIG. 11 is a schematic view of a sync detector circuit used in an embodiment of the invention.
Figure 12:
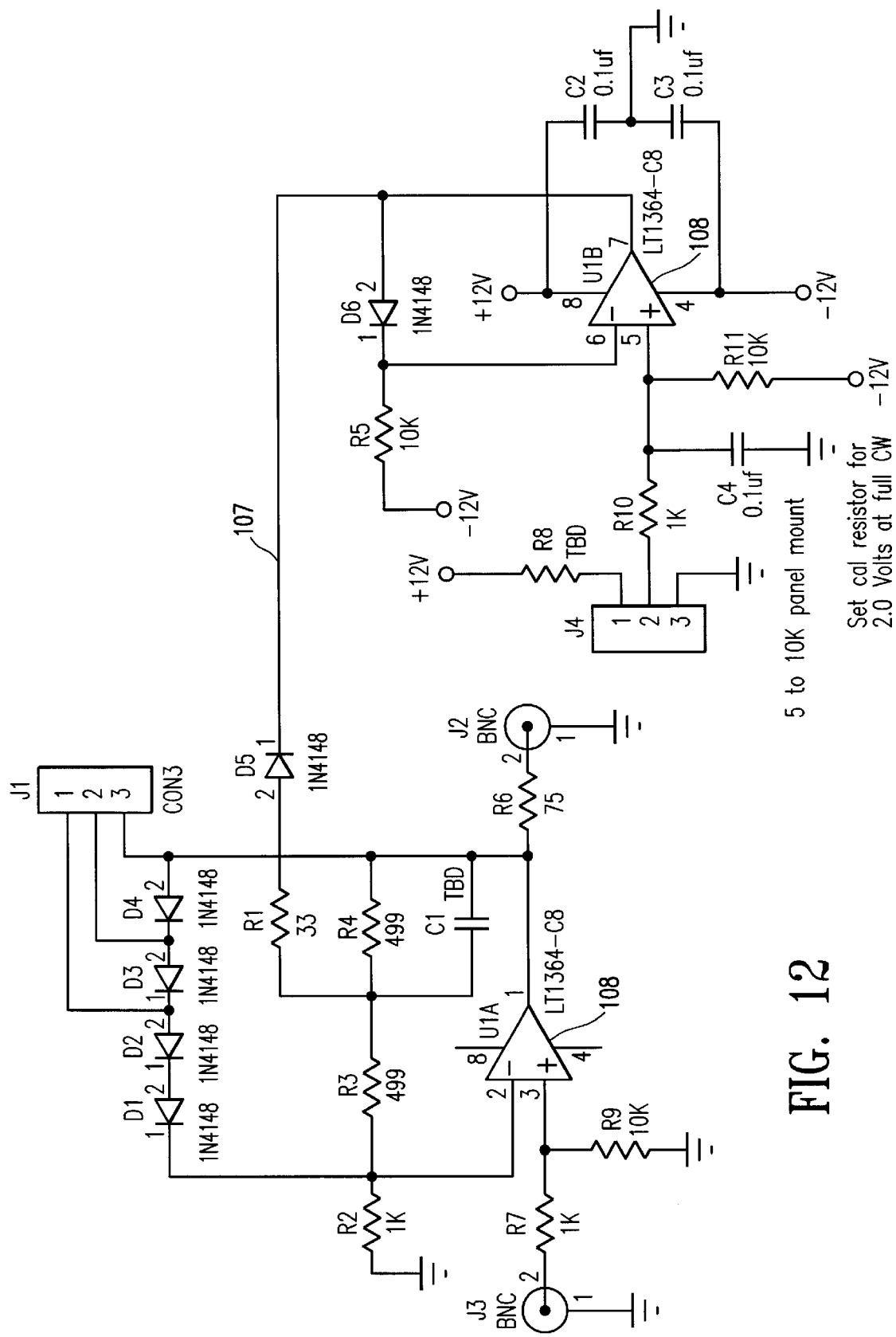
FIG. 12 is a schematic view of a contrast enhancement circuit used in an embodiment of the invention.
Figure 13:
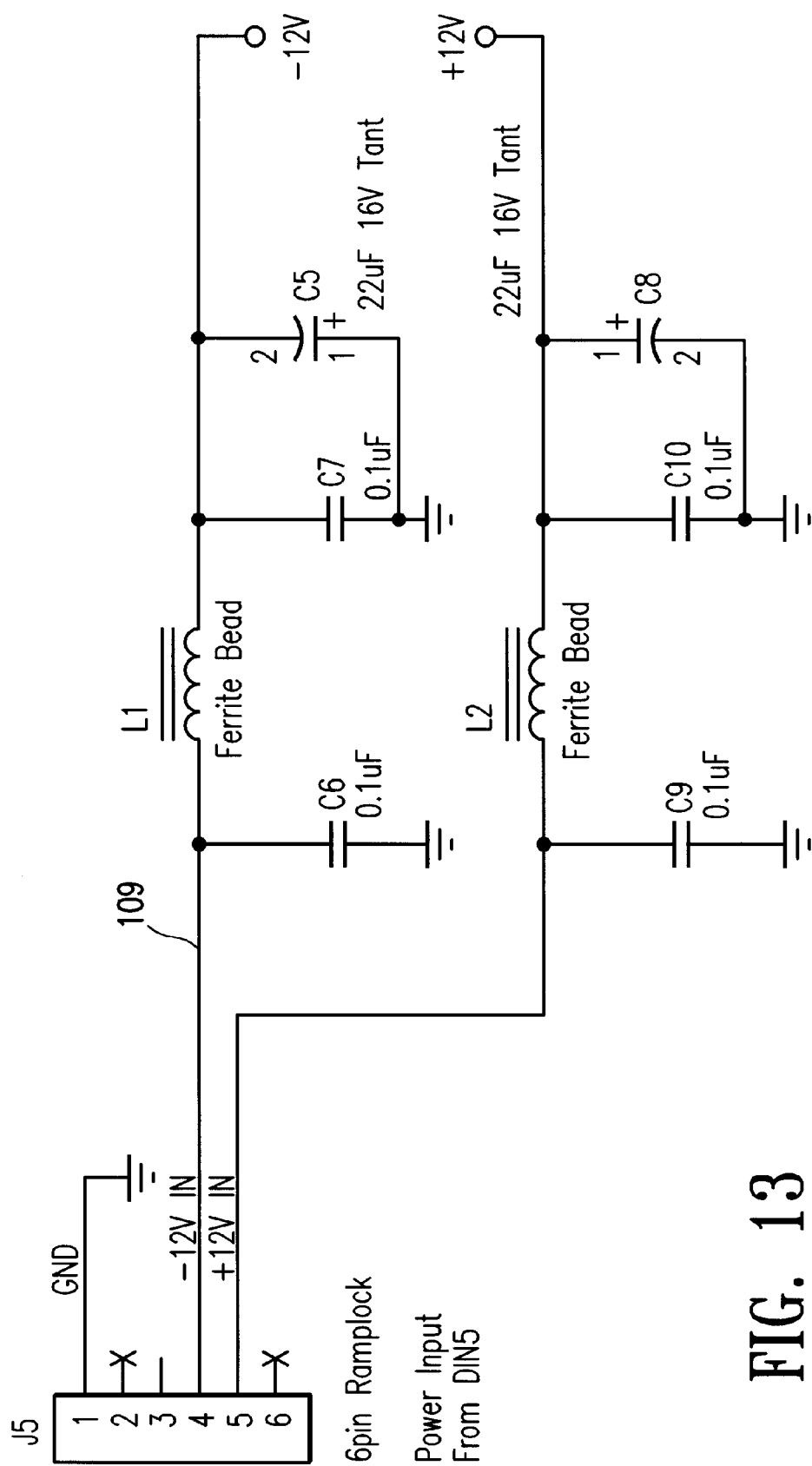
FIG. 13 is a schematic view of a power supply circuit used in an embodiment of the invention.

FIGS. 11–13 are schematic views of various circuits used in an embodiment of the invention. FIG. 11 illustrates a sync detector circuit 105 incorporating an integrated circuit 106 model LM1881 manufactured by National Semiconductor. FIG. 12 shows a contrast enhancer circuit 107 which uses an op-amp 108 model LT1364-C8 manufactured by Linear Technology. FIG. 13 illustrates a power supply 109. The circuit illustrations are coupled and bussed together generally as indicated at the connectors shown in the figures.

FIG. 14 illustrates the secondary video monitor 17 and sensor boards 26 disposed on the screen 17A thereof shown in FIG. 1. The sensor boards 26 are preferably adjustably secured in a position adjacent the screen 17A of the secondary video monitor 17 such that the photo diodes 79 on the sensor boards 26 can receive light from the image displayed on the screen 17A. An interference bar acquisition device 18 is coupled in communication with the sensor boards 26 and receives digital data from the sensor boards 26 indicating whether a light signal above threshold value was detected by each individual photodiode 79. The sensor boards 26 as shown each have 8 photodiodes 79 operating in the visible to infrared light wavelengths, however, any suitable photodiode 79 can be used. Examples of detectors that could be used for the purpose of the diodes 79 include PIN diodes, photodiodes, phototransistors and the like.

Figure 16:
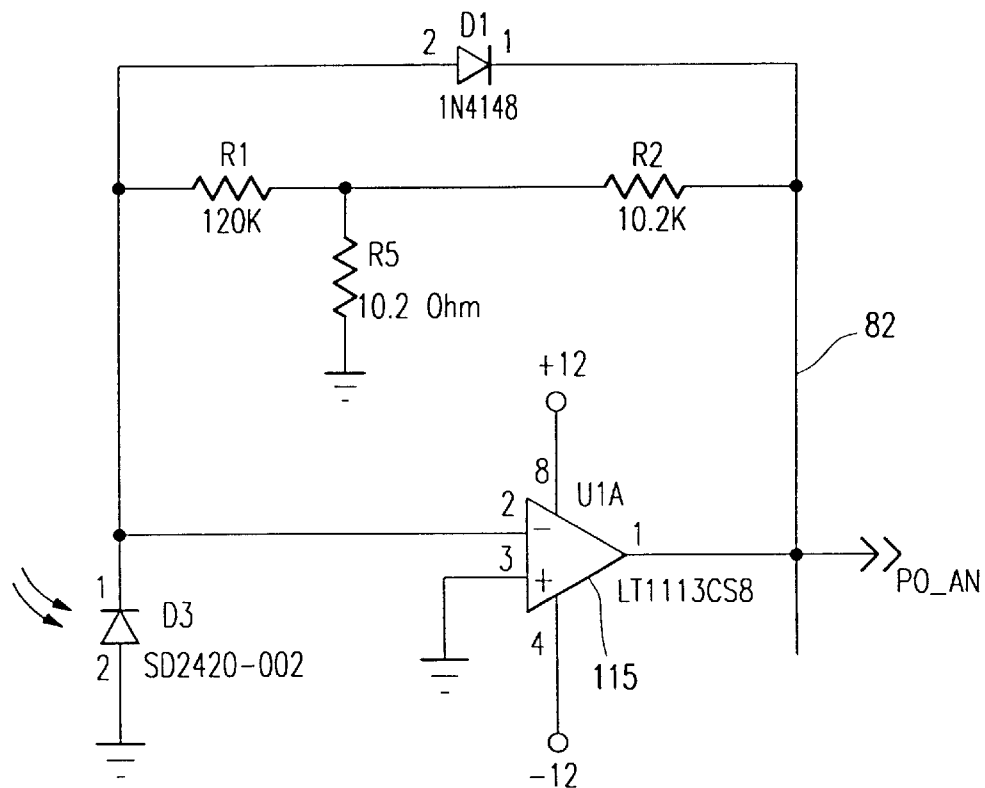
FIG. 16 is a schematic view of a diode signal amplifier which can be used on an embodiment of the sensor boards shown in FIGS. 14 and 15.
Figure 17:
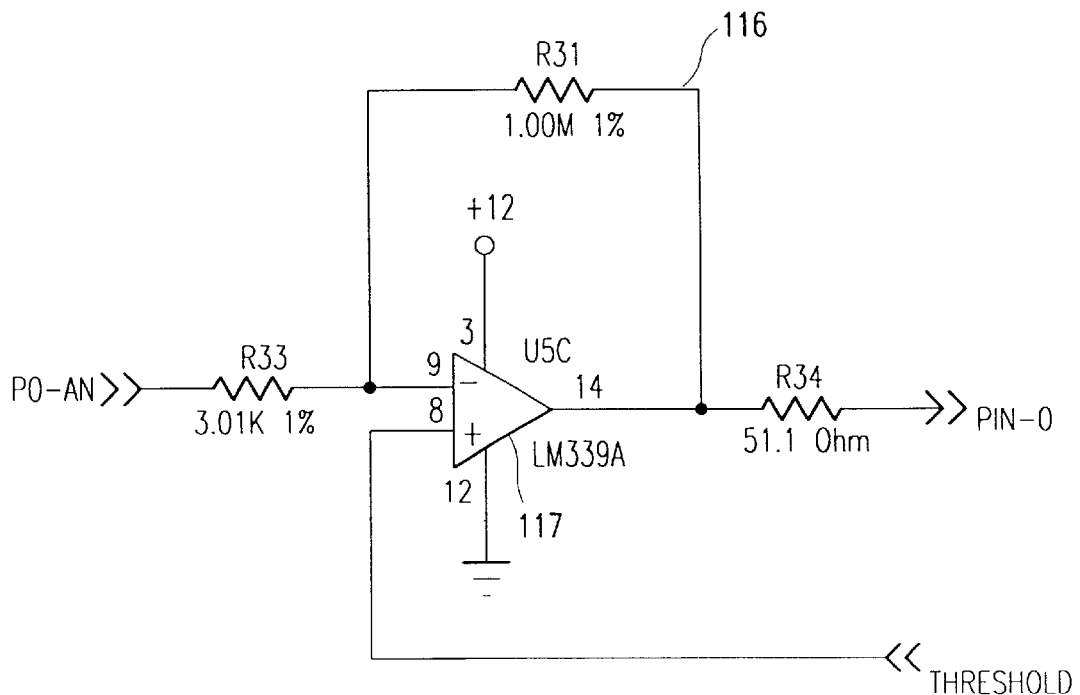
FIG. 17 is a schematic view of a DC level comparator circuit which can be used on an embodiment of the sensor boards shown in FIGS. 14 and 15.

FIG. 15 is a further enlarged view of a portion of one of the sensor boards 26 shown in FIG. 14. The photodiodes 79 are coupled to diode signal amplifiers 82 and the diode signal amplifiers 82 are in turn coupled to DC level comparators 83. An embodiment of a diode signal amplifier 82 is illustrated in FIG. 16. The amplifier 82 uses a low offset precision FET input op-amp 115, model LT1113CS8, manufactured by Linear Technology. FIG. 17 illustrates a specific embodiment of a DC level comparator circuit 116 suitable for use with the invention. The DC level comparator utilizes a high speed voltage comparator 117 in the circuit as shown, which is a model LM339A, manufactured by National Semiconductor.

Figure 18:
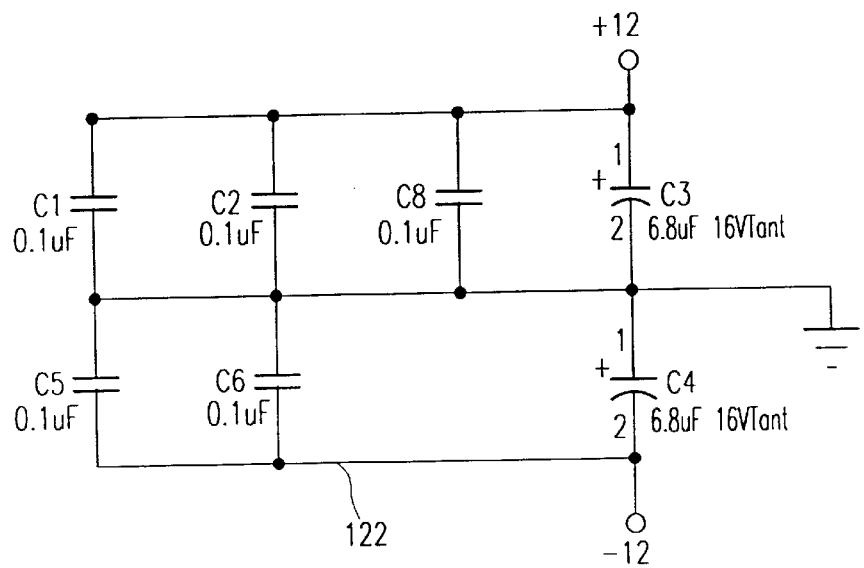
FIG. 18 is a schematic view of a power supply decoupling circuit which can be used in an embodiment of the invention.
Figure 19:
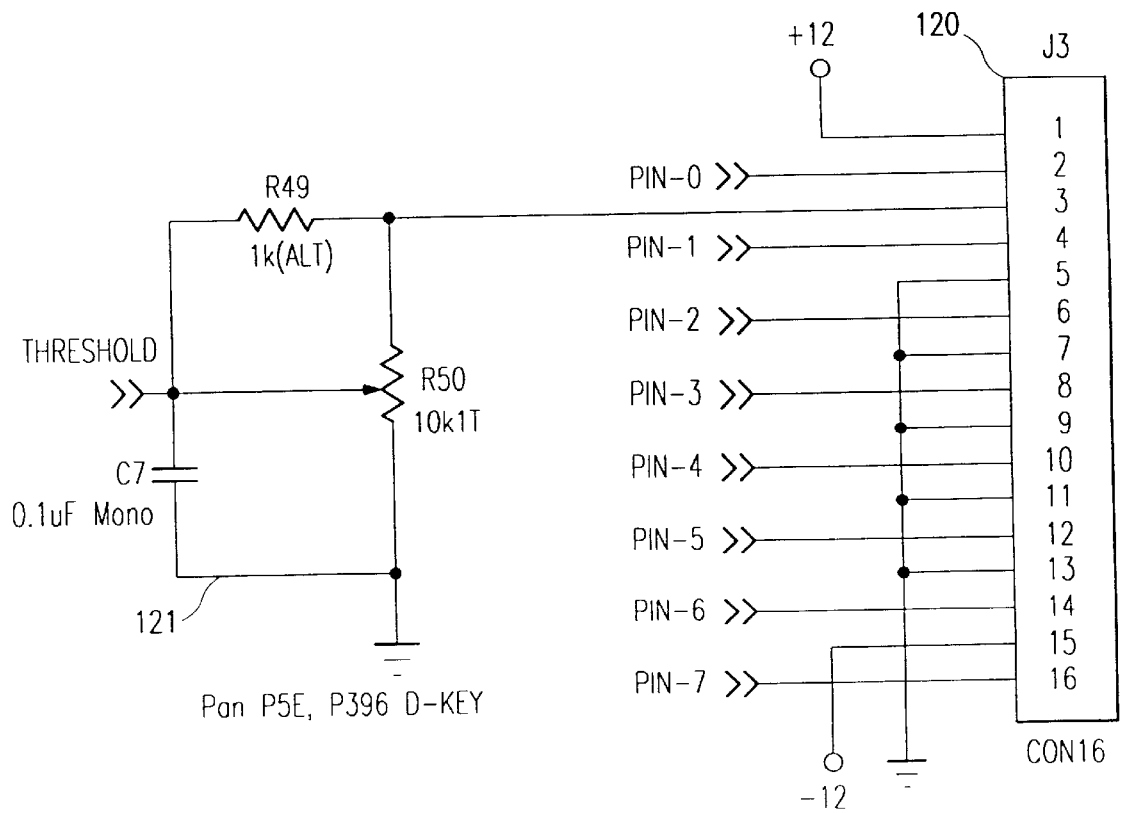
FIG. 19 is a schematic view of a connector bus and threshold adjust circuit that can be used for the sensor boards shown in FIGS. 14 and 15.
Figure 20:
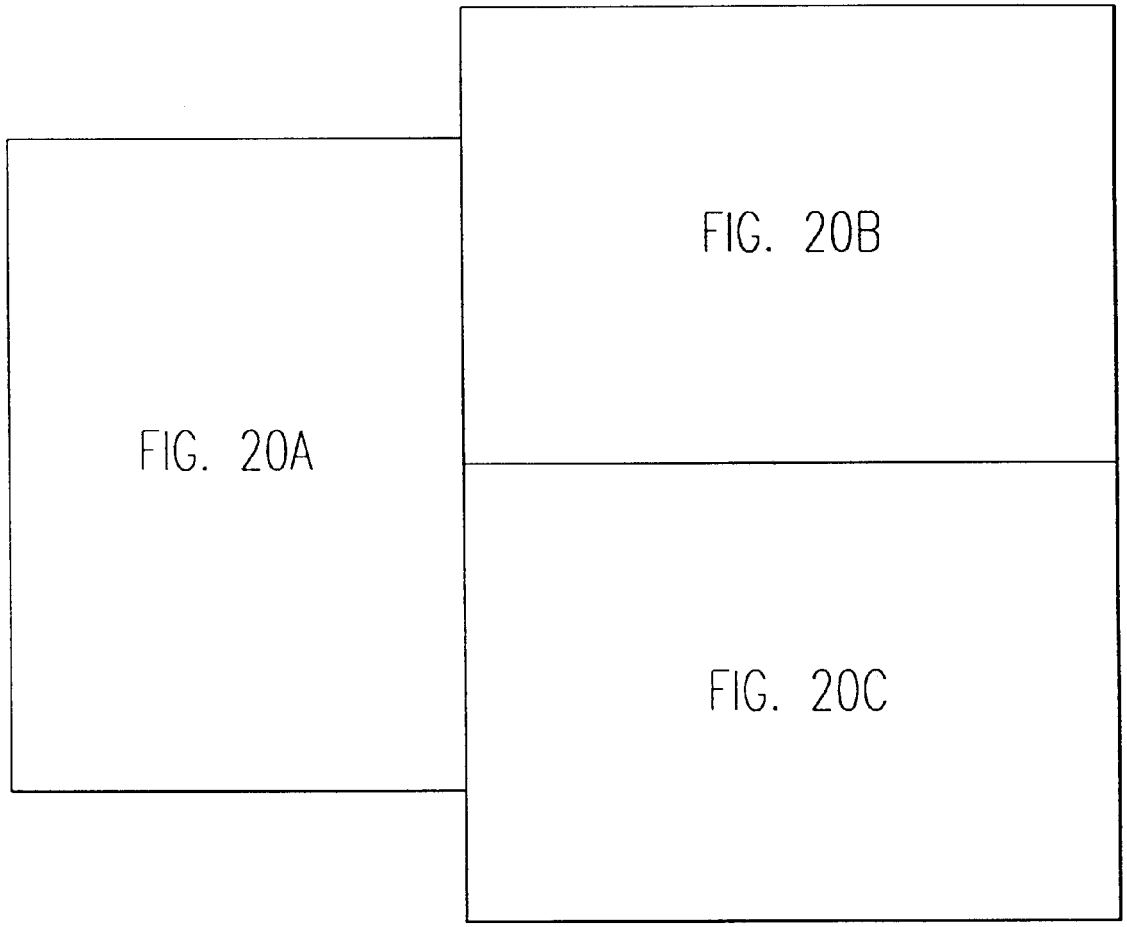
FIG. 20 is a schematic view of a programmable logic device which can be used with an embodiment of the invention.
Figure 20B:
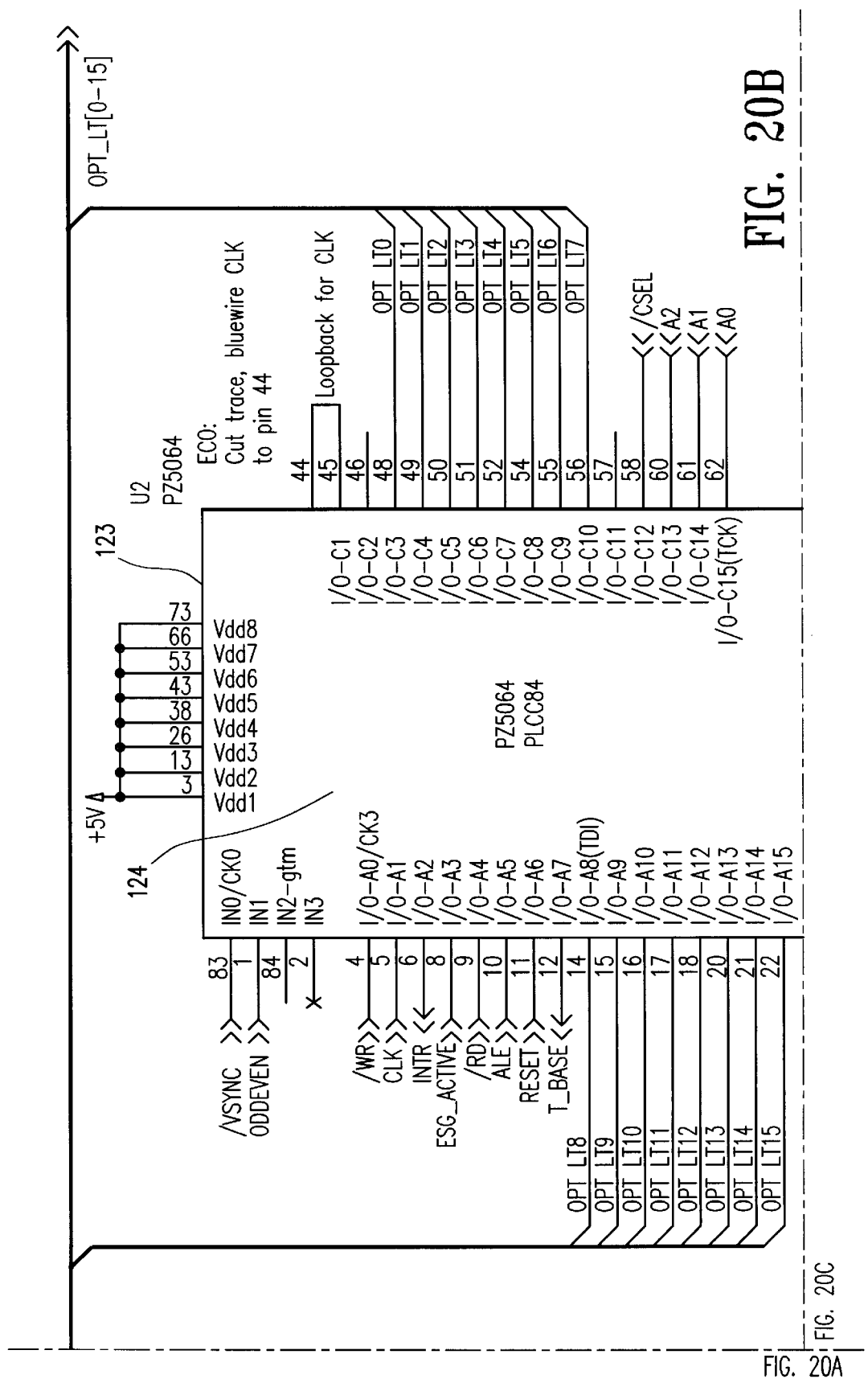
Figure 20C:
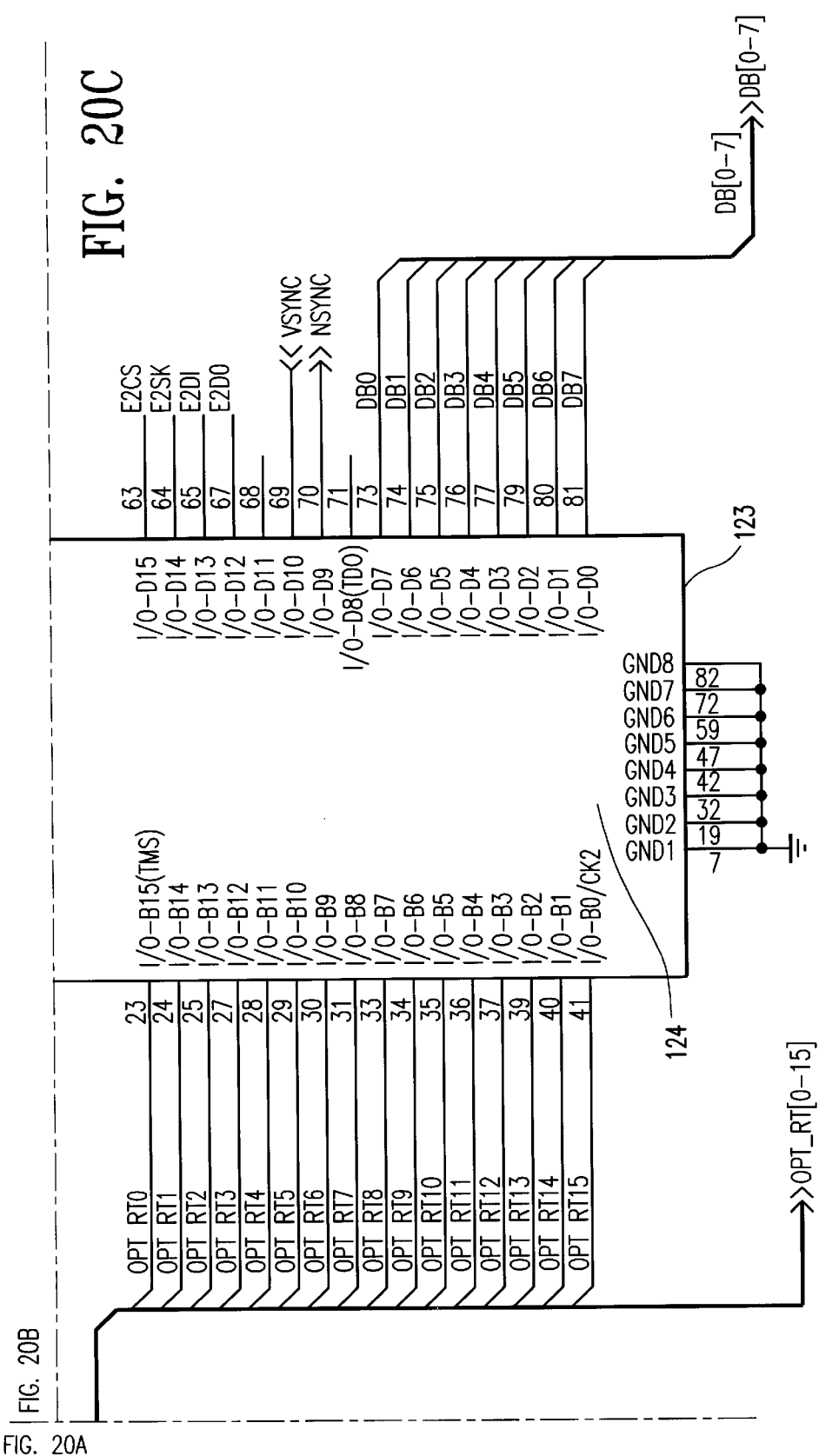

FIGS. 18–29 illustrate various circuit elements suitable for use with an embodiment of the invention as shown. FIG. 19 shows a connector bus 120 for the sensor boards 26 including a board sensitivity calibration circuit 121. Also shown in FIG. 18 is a power supply decoupling circuit 122. FIG. 20 shows an embodiment of an interference bar acquisition device 123 which consists of a complex programmable logic device integrated circuit 124. The embodiment of FIG. 20 utilizes a Phillips/Xilinx PZ5064 programmable logic device, however, any suitable device having similar capability could be used.

Figure 21:
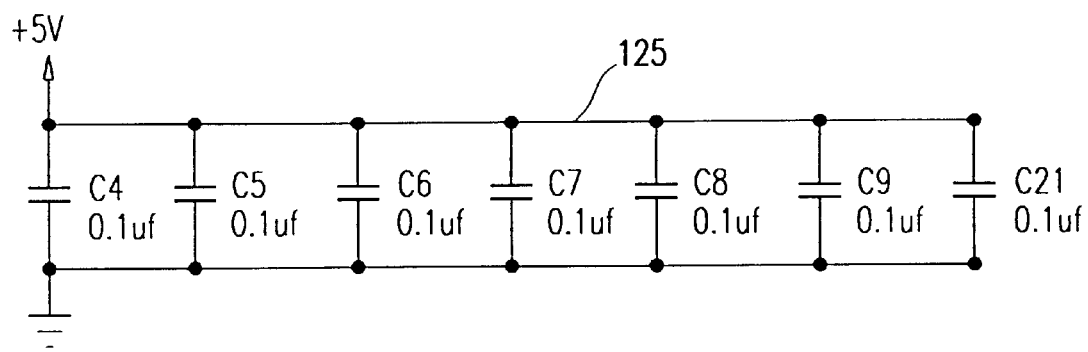
FIG. 21 is a schematic view of a power supply decoupling circuit which can be used with an embodiment of the invention.
Figure 22:
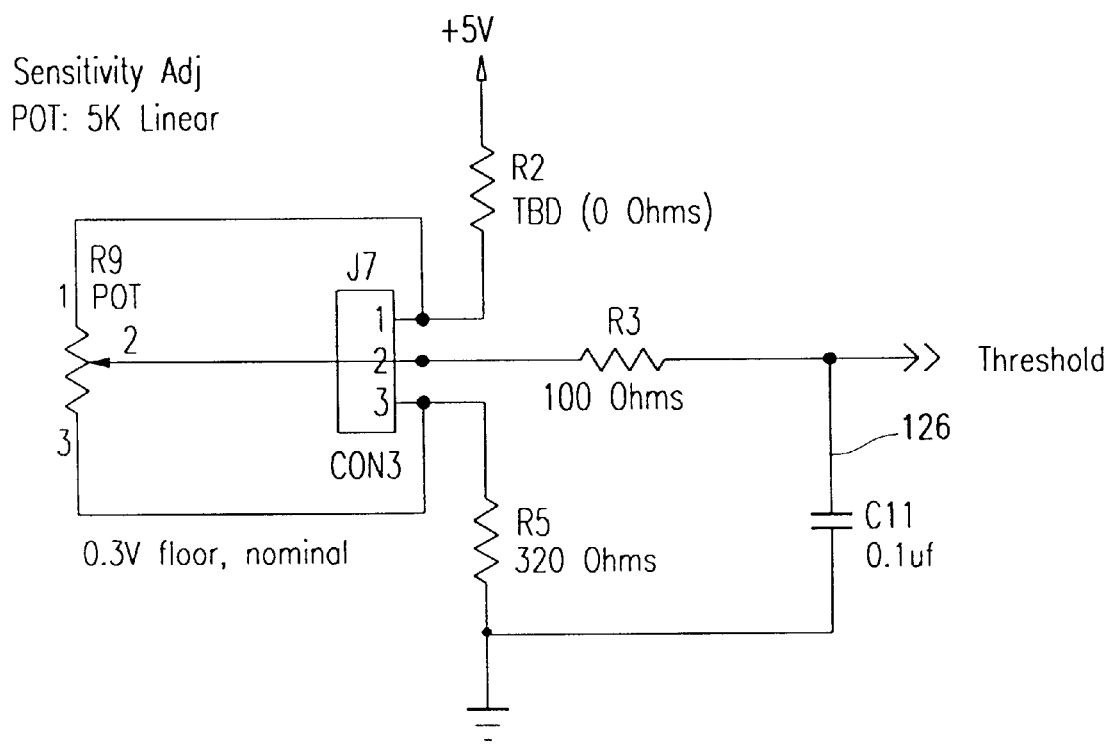
FIG. 22 is a schematic view of a threshold adjustment circuit which can be used with an embodiment of the invention.
Figure 23:
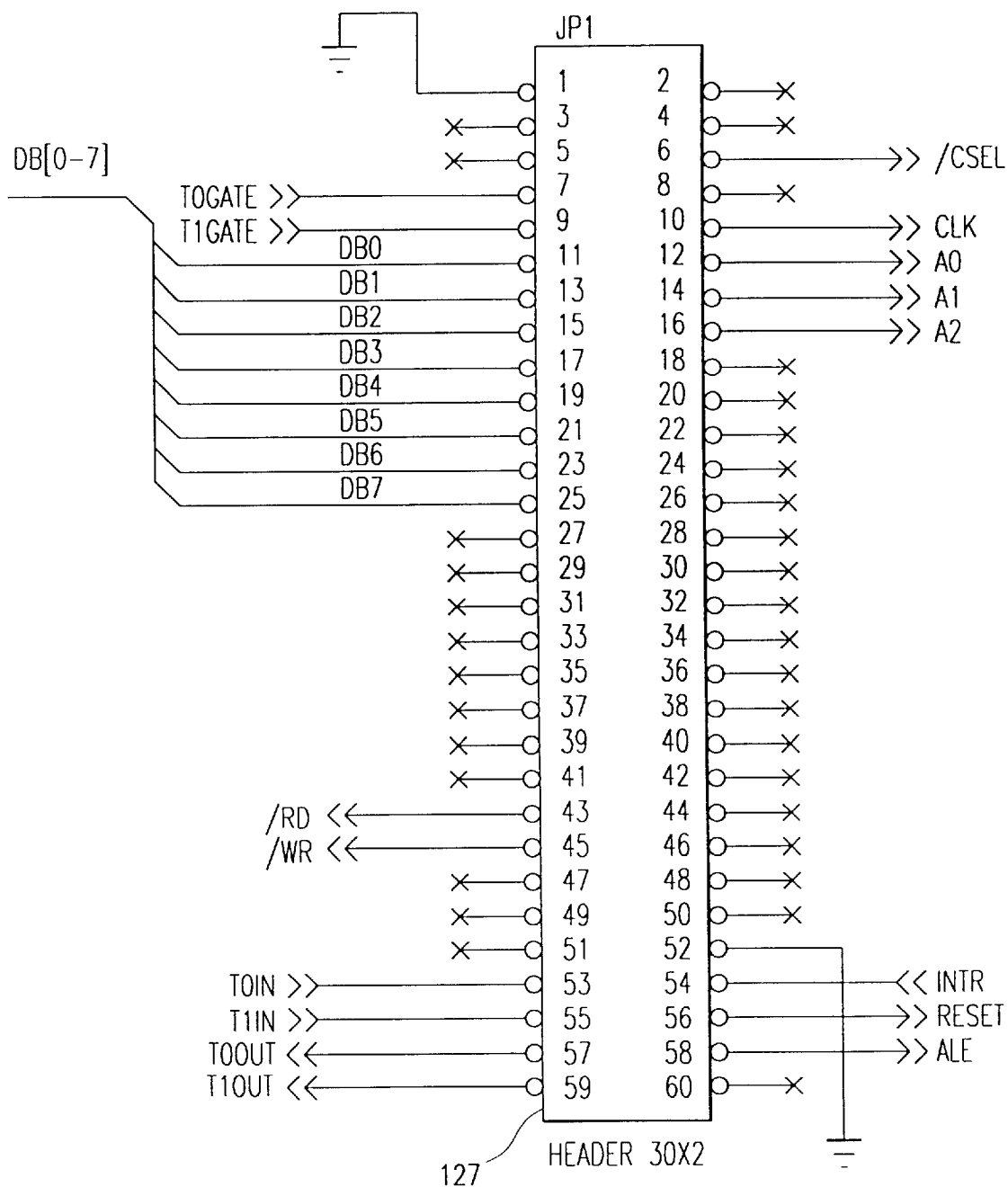
FIG. 23 is a schematic view of a processor bus connector which can be used with an embodiment of the invention.
Figure 24:
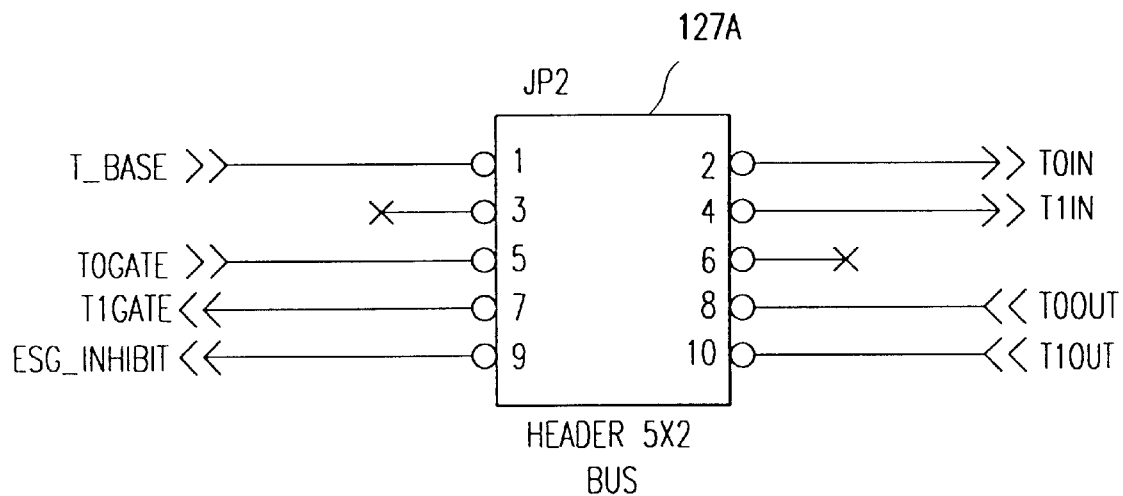
FIG. 24 is a schematic view of a configuration jumper which can be used with an embodiment of the invention.
Figure 25:
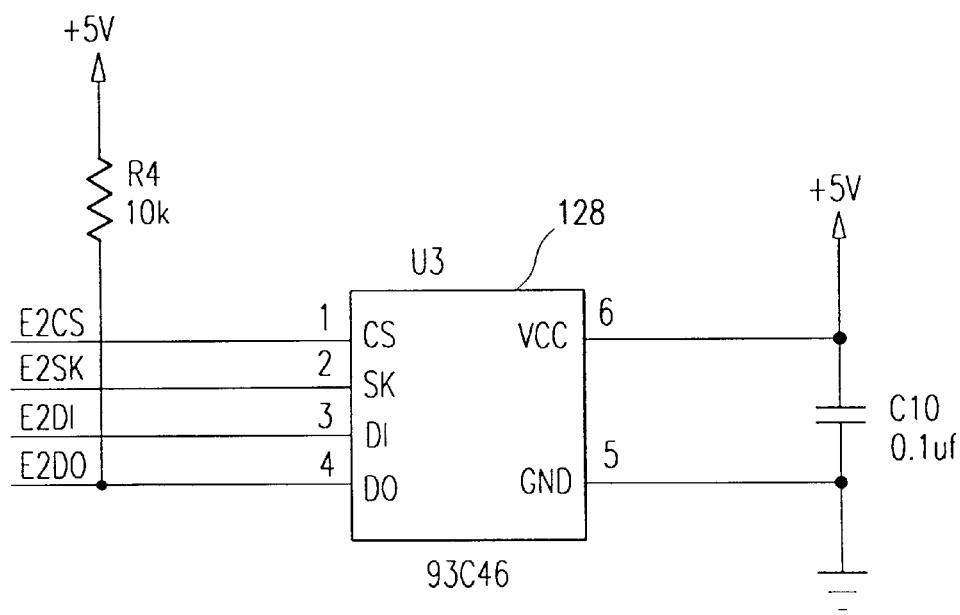
FIG. 25 is a schematic view of an erasable programmable ROM which can be used with an embodiment of the invention.
Figure 26:
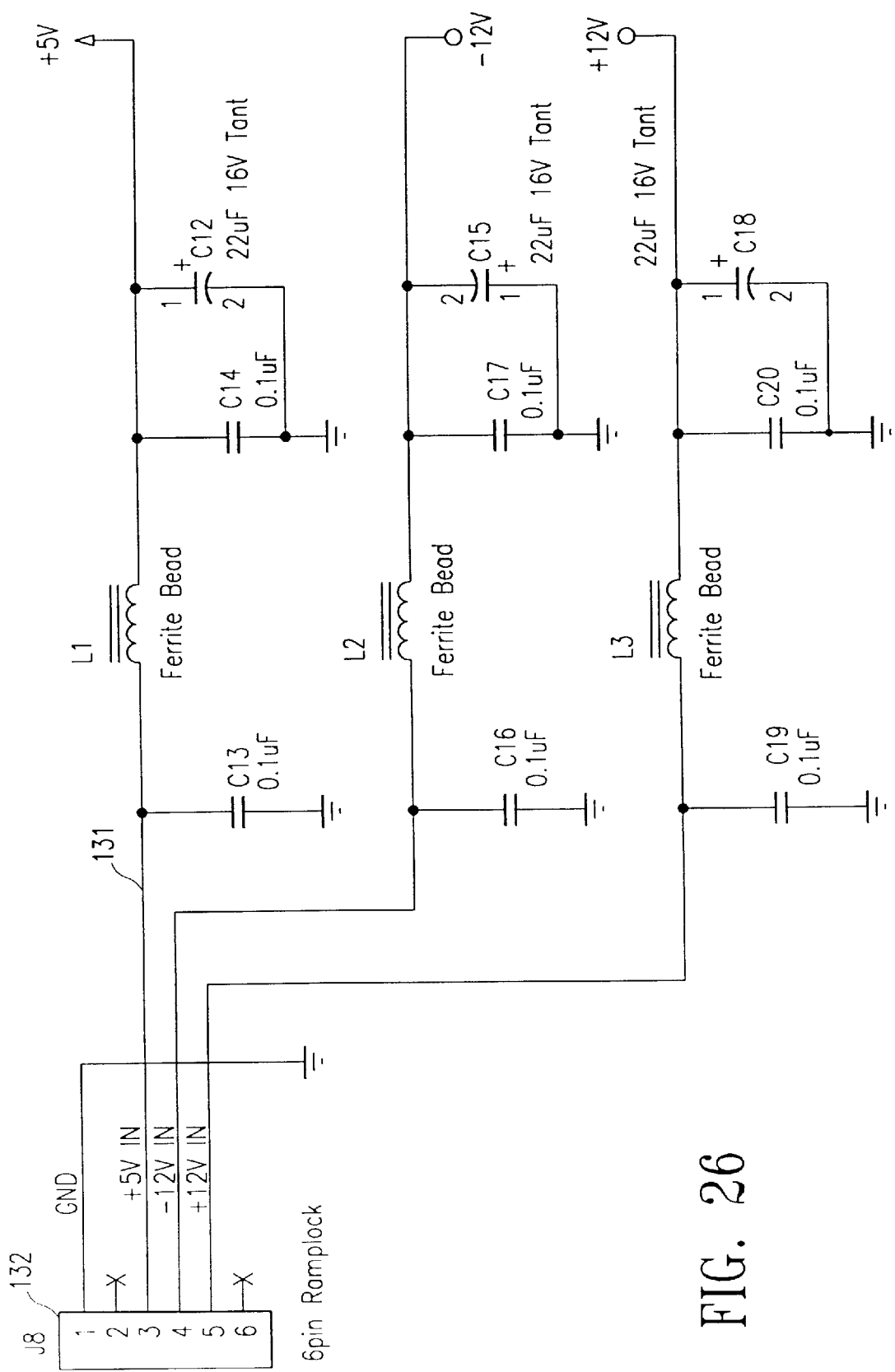
FIG. 26 is a schematic view of a power supply circuit which can be used with an embodiment of the invention.
Figure 27:
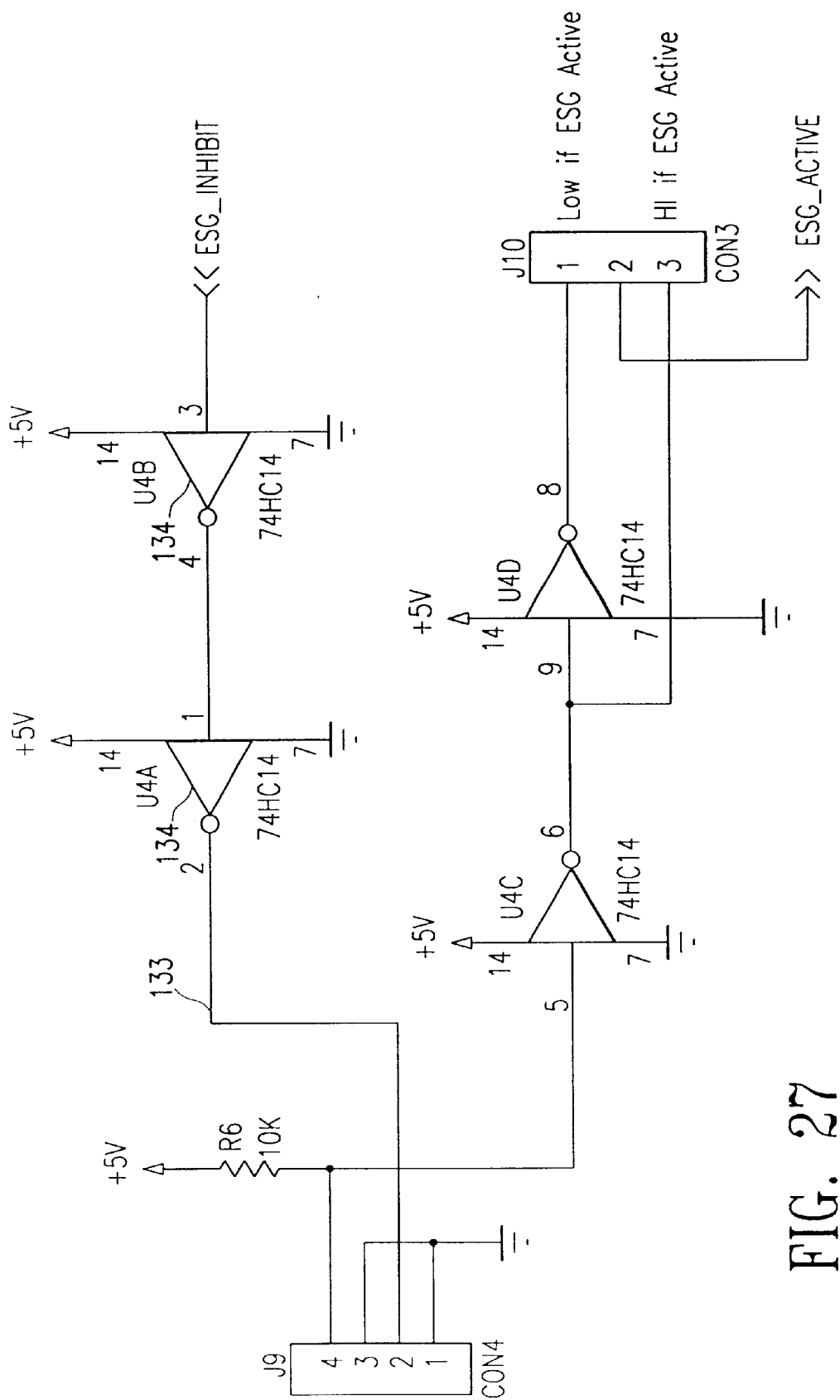
FIG. 27 is a schematic view of an ESG interface circuit that can be used with an embodiment of the invention.

FIG. 21 shows a power supply decoupling circuit 125 and FIG. 22 illustrates a threshold adjustment circuit 126 used to adjust the sensitivity of the photo diodes 79 used on the sensor boards 26. FIG. 23 illustrates a bus 127 for the I.C. 124 and FIG. 24 illustrates a programming jumper block 127A. FIG. 25 shows an erasable programmable read only memory, preferably an electrically erasable programmable read only memory (EEPROM) device 128. The EEPROM 128 shown in FIG. 25 is a model 93C46 manufactured by National Semiconductor. FIG. 26 is a power supply circuit 131 connected at connector 132 as indicated. FIG. 27 illustrates an embodiment of an ESG interface circuit 133 which incorporates a CMOS hex Schmidt Trigger inverter 134, model 74HC14.

Figure 28:
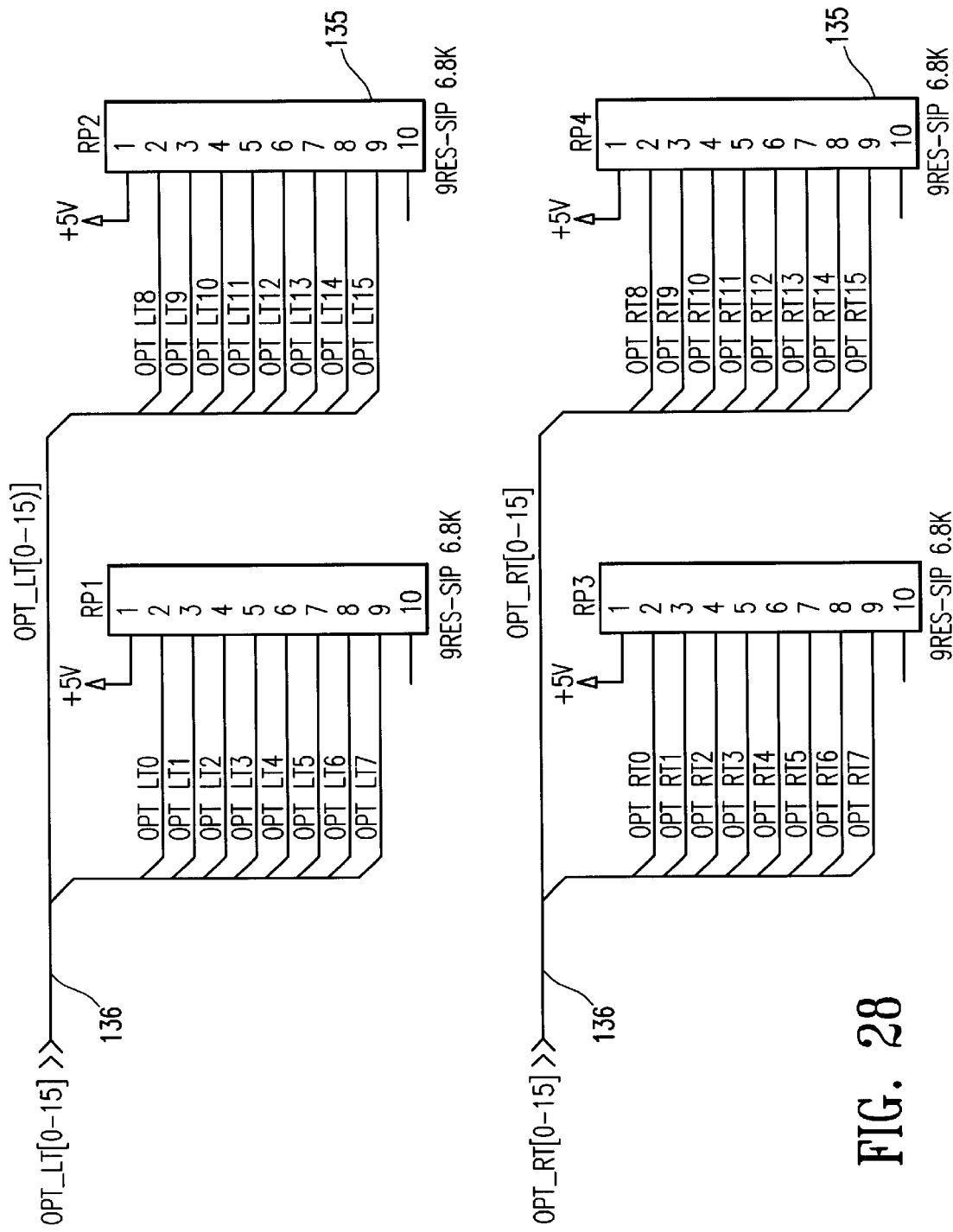
FIG. 28 is a schematic view of two sets of resistor pack circuits that can be used with an embodiment of the invention.
Figure 29:
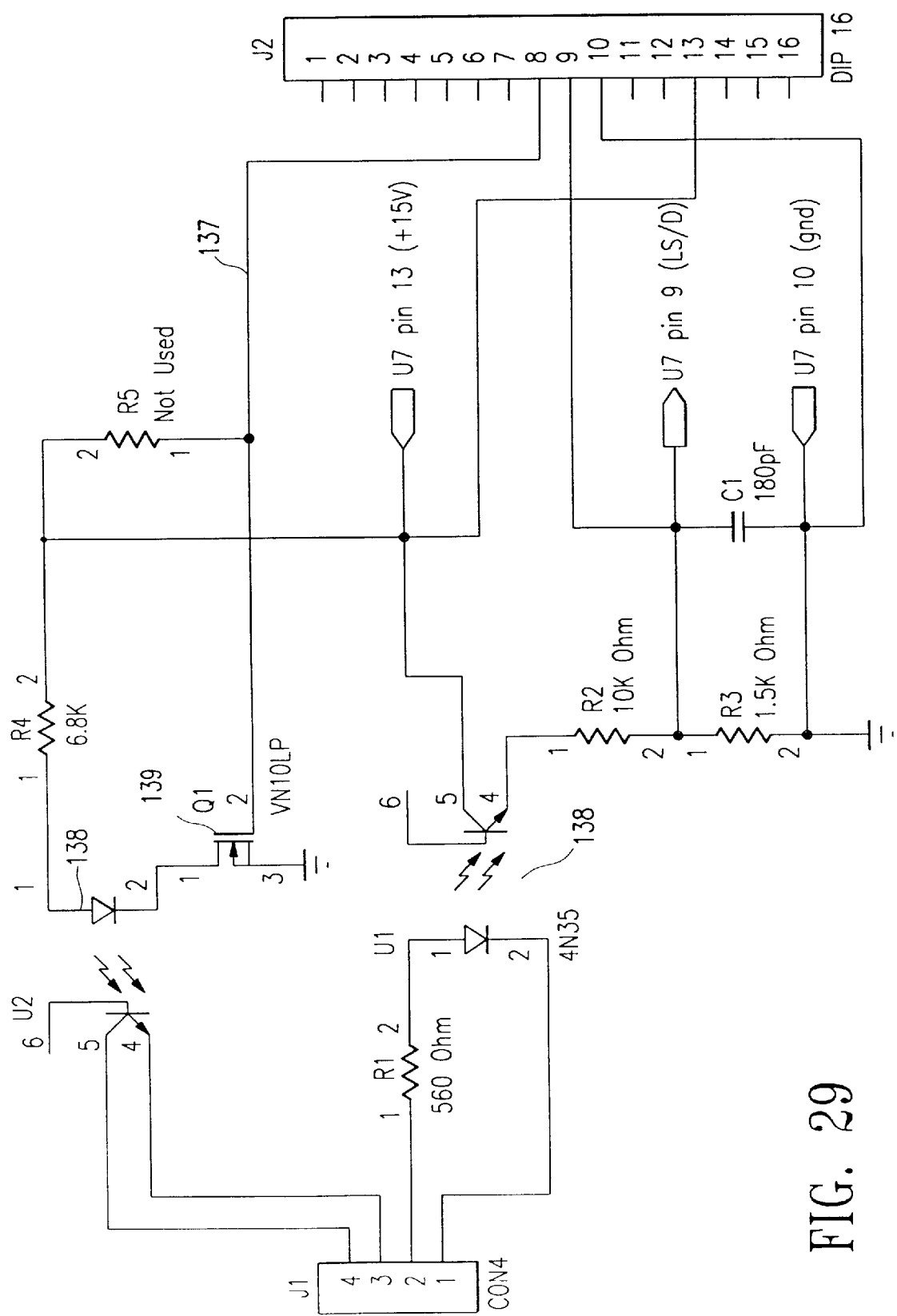
FIG. 29 is a schematic view of an internal ESG inhibitor circuit with optical isolation that can be used with an embodiment of the invention.

FIG. 28 shows two resistor packs 135 used at terminal connections 136 of the programmable logic device 124. FIG. 29 depicts an internal inhibitor circuit 137 with optical isolation carried out with high isolation voltage opto isolators 138. The internal inhibitor circuit 137 also includes a low threshold voltage n channel mosfet 139, model VN10LP, manufactured by Zetex Corporation.

Figure 30:
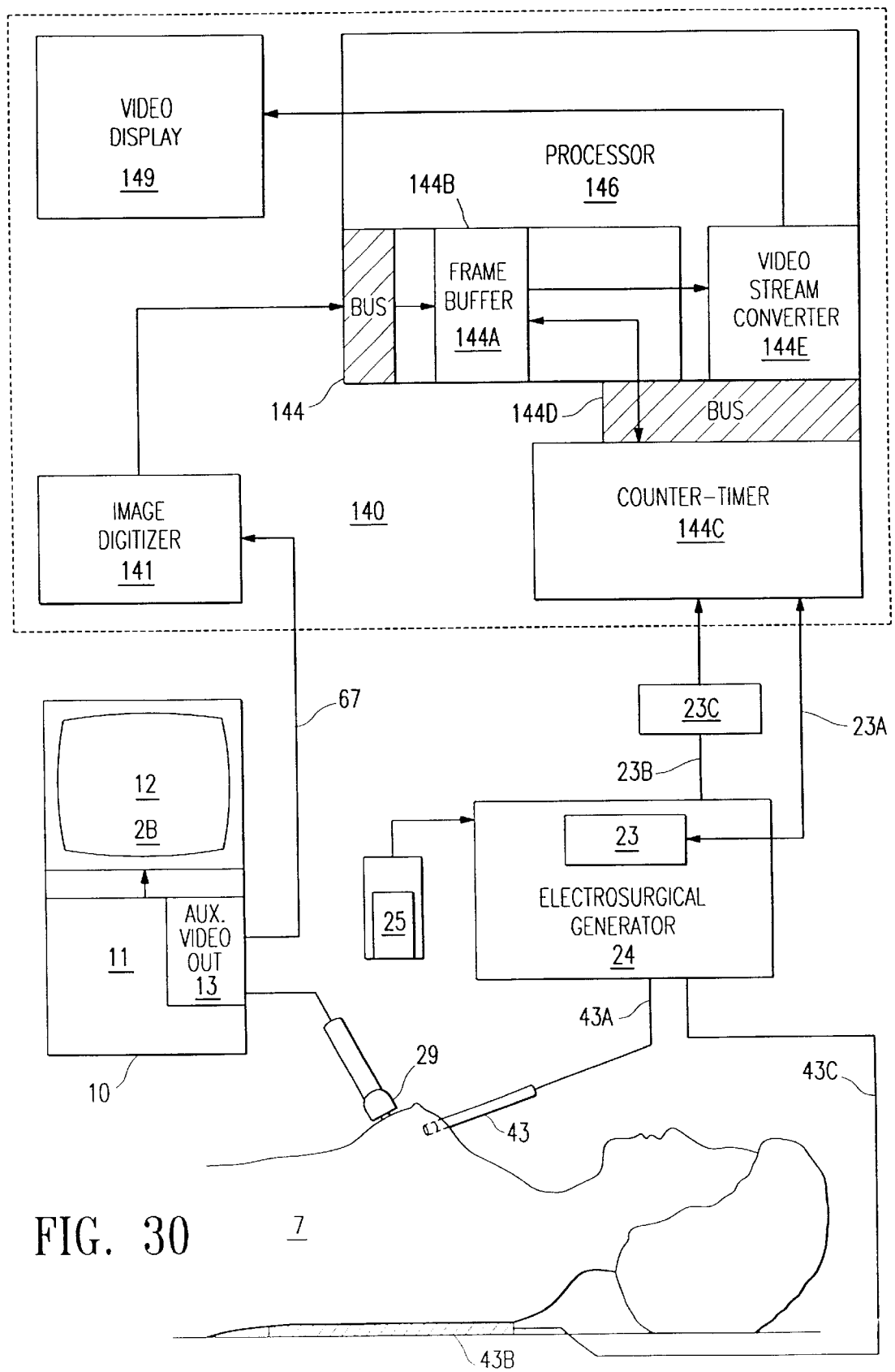
FIG. 30 shows a side elevational view of a patient and a schematic block diagram of an ultrasonic imaging, an electrosurgical instrument, and an embodiment of an interference reduction system having features of the invention.

FIG. 30 illustrates an alternative embodiment of an interference reduction system 140 having features of the invention. The embodiment of the interference reduction system 140 shown in FIG. 30 operates in a similar fashion to the embodiment of the interference reduction system 9 shown in FIG. 1. The primary difference between the interference reduction system 9 and the interference reduction system 140 lies in the manner in which an interference bar is detected and characterized. In the embodiment of FIG. 1, the interference bar is detected by photo diodes 79 placed adjacent the screen 17A of a secondary video monitor display 17. The interference reduction system 140 of FIG. 30 carries out the same function with the use of a frame grabber device or image digitizer 141 which digitizes the video stream signal from the ultrasonic imaging system 142.

As shown in FIG. 30, ultrasonic imaging system 10 includes a transducer 29 which is in contact with patient 7. An electrosurgical generator (ESG) 24 is electrically coupled to an electrosurgical probe 43. The ESG 24 can be activated by a footswitch 25, which upon activation, operates nominally at a starting frequency, phase and duty factor set by processor 146 and regulated by an internal inhibitor 23 via a counter-timer 144C. The status of the footswitch 25 is communicated to processor 146 via an electrical conduit 23B and footswitch status interface 23C.

The internal inhibitor 23 is coupled to a counter-timer 144C by a timebase signal conduit 23A. The counter-timer 144C also communicates with the processor 146 through a bus 144D. When the ESG 24 is operated at the same time as the ultrasonic imaging system 10, electrical and electromagnetic noise can result in the creation of an interference bar, such as interference bar 54 described above, which is embedded in the image data generated by the ultrasonic imaging system 10. The mechanism for the creation of the interference bar for the embodiment of the invention shown in FIG. 30 can be the same mechanism as that discussed above with regard to the embodiment of the invention shown in FIG. 1, and generally illustrated in FIGS. 2–7 and described in the corresponding portions of the detailed description.

Figure 32:
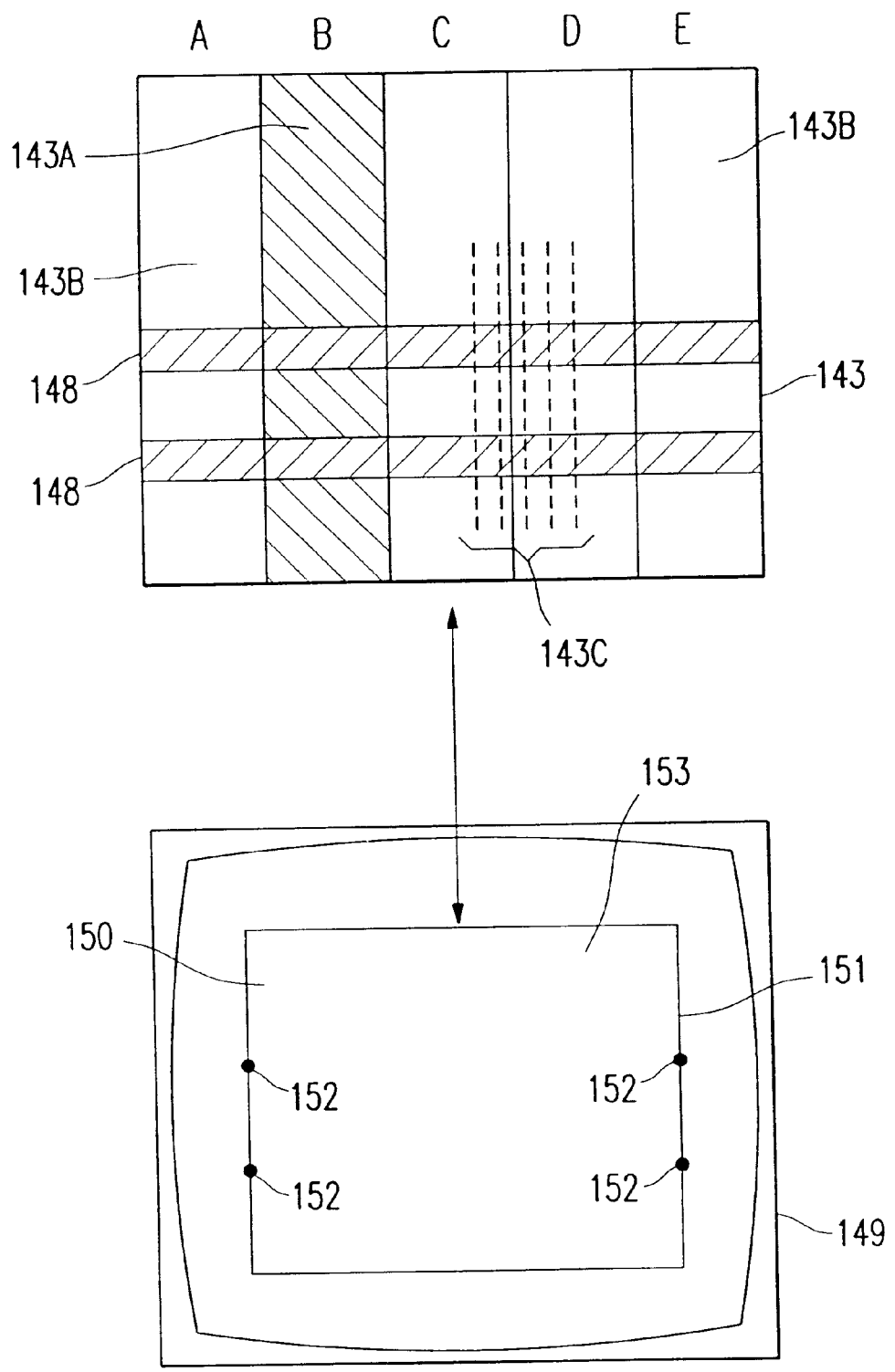
FIG. 32 is a block diagram view of an image frame and the corresponding video image display wherein the interference analysis zones are shown on the image frame and cursors representing the positions of the interference analysis zones are shown on the screen of the video monitor display.

The data representing a digitized image frame 143 containing an interference bar 143A generated by the image digitizer 141, as shown in FIG. 32, is communicated through a bus 144 then stored to a frame buffer 144A which can be disposed within the RAM 144B a processor 146. The processor 146 can then read and analyze the stored digitized image 143 to determine whether an interference bar 143A exists in the image frame 143. If an interference bar 143A exists in any given image frame 143, the processor 146 can then perform a similar analysis on adjacent image frames in the image buffer 144A to locate the position of the interference bar 143A therein and calculate the position and velocity of the interference bar 143A from the difference in position of the interference bar in successive image frames 143. In the course of the analysis of the image frame 143 in the frame buffer 144A, the processor 146 may at any appropriate time forward the image data of the image frame 143 from the frame buffer 144A to a video stream converter 144E to convert the digitized image to a video data stream and to display the converted image frame on the optional user interface video display 149.

Figure 31:
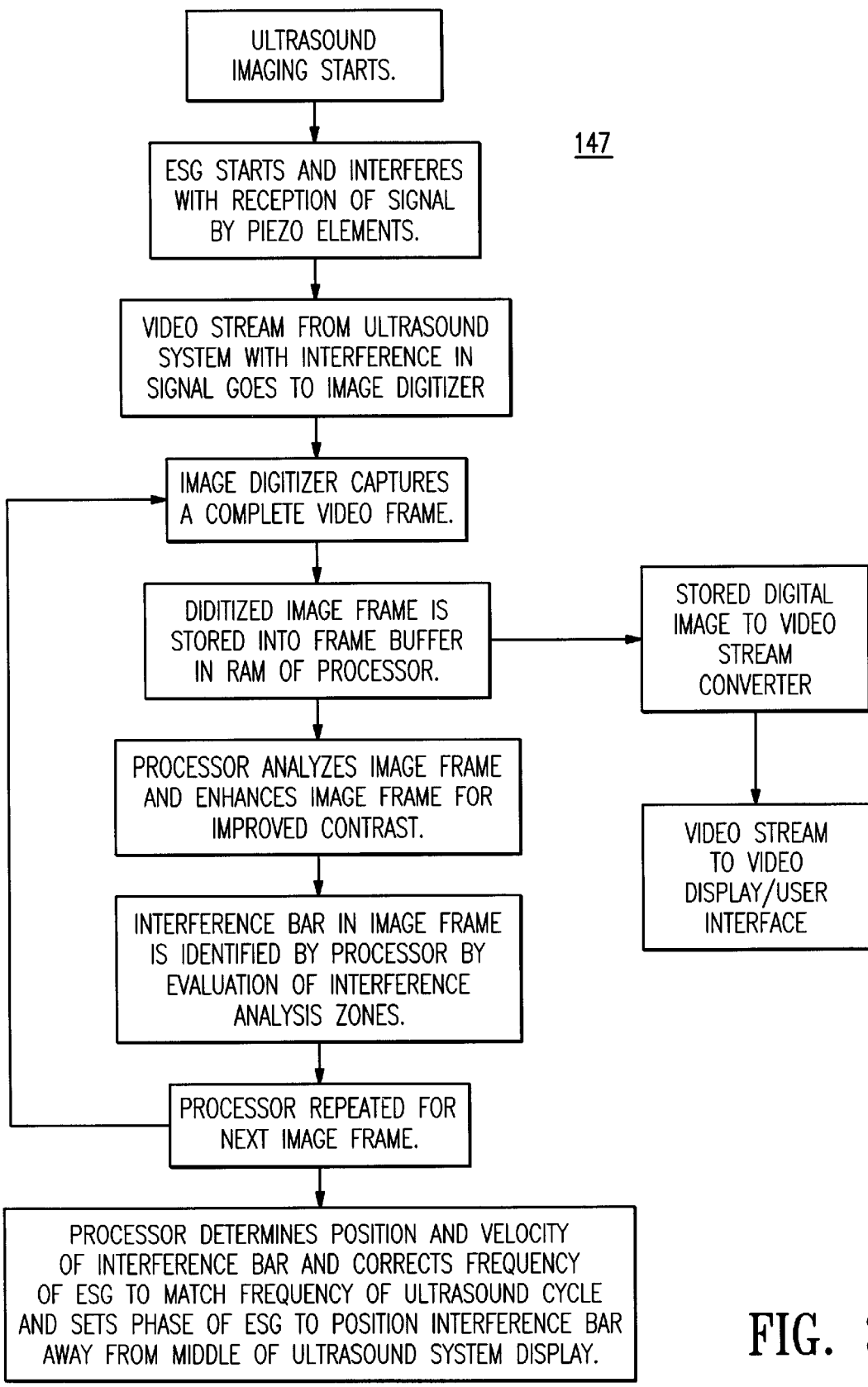
FIG. 31 is a flowchart of some of the processes of the embodiment of the invention illustrated in FIG. 30 for adjusting the frequency and phase of the intermittent operation of an electrosurgical generator in order to fix the position of an interference bar in a desired location within an image frame.

Once the processor 146 determines the position and velocity of the interference bar 143A within the stored image frame 143, the processor 146 can then use this information to determine the difference in frequency and phase of the time gated operation of the ESG 24 and the frequency and phase of the ultrasonic imaging cycle that generated the image frame 143. From the calculated difference in frequency and phase, the adjustment necessary to match the frequency and phase of the ESG operation cycle to the frequency and phase of the ultrasonic imaging cycle can be determined. This can be done in one adjustment step, or preferably, it is done in a series of iterative steps such as described above with regard to the embodiment of FIG. 1. The position of the interference bar 143A can be locked in a desired position in subsequent image frames 143, such as in the lateral extremities 143B of the image frame 143, so as not to obscure the operator's view of the displayed video image 150 and 12B. An example of a sequence for the operation of the interference reduction system 140 shown in FIG. 30 can be found in the flowchart 147 of FIG. 31.

FIG. 32 illustrates an example of a stored image frame 143 with interference bar 143A positioned at column B of the image frame and with interference analysis zones 148 indicated on the frame 143. The interference analysis zones indicate scan lines along which the processor 146 may look at each pixel of the image frame 143 to determine whether or not an interference bar 143A exists in the image frame 143 of interest. Assuming sufficient speed of the processor 146 and ancillary hardware, the processor 146 can scan and analyze the entire stored image frame 143 image frame pixel by image frame pixel to determine the presence and position of an interference bar 143A within the image frame 143. However, it has been shown to be practical and computationally faster to merely scan two interference analysis zones 148 or lines in a manner similar to the method used with the two linear arrays of diodes 79 on the sensor boards 26 of the interference reduction system 9 illustrated in FIG. 1.

The interference analysis zones 148 typically encompass a line across the image frame 143 that is one image frame pixel thick and extends across the entire image frame 143. This can encompass about 50 to about 500 pixels per analysis zone 148, preferably about 250 to about 350 pixels per analysis zone 148. A voting system and method can then be employed based on image frame pixel zones 143C which can be polled and analyzed in a similar fashion to the polling of the diodes 79 of the sensor board diode zones 26A described above. The voting, polling and computations in system 140 can take place within the processor 146 without the need for external sensor boards 26 and secondary video display 17. In addition the voting and computational process carried out by processor 146 in making the determination of the existence and position of an interference bar 143A can essentially follow the voting and computational processes of processor 19 shown in FIG. 1. Note that the image frame pixel zones 143C as shown in FIG. 32 extend across only a portion of the image frame 143, however, the image frame pixel zones preferably would be defined and polled across the entire width the image frame 143 and interference bar analysis zones 148.

The optional user interface video monitor display 149 at the bottom of FIG. 32 shows an outline 151 of the stored image frame 143 above it with four cursors 152 which indicate to the operator setting up the machine where within the image frame 143 the processor 146 will be analyzing and scanning in order to detect the presence of an interference bar 143A. Typically, the interference analysis zones 148 will be positioned at the bottom of the image frame 143 as the bottom of the image frame corresponds to the far field of the image which may be of less interest to the operator of the device. The contrast tends to be better in that portion of the image frame 143 because often the operator, being less interested in that far field portion of the image, manually adjusts the brightness in that portion of the image to a low setting. The top of the screen 153 corresponds to the near field tissue which is closest to the ultrasonic transducer 29 and tends to be of greater interest to the operator, particularly in a breast biopsy procedure. A darker screen 151 on average in the absence of an interference bar 143A improves the contrast between the interference bar 143A and the screen background, thereby improving the contrast and resolution of the interference bar detection process. In one embodiment, processor 146 can be a Pentium 533® MHz operating on MS DOS in a personal computer housing. The image digitizer 141 can be an Mvision 500 Series Frame Grabber manufactured by Mutech Corporation.

Figure 33:
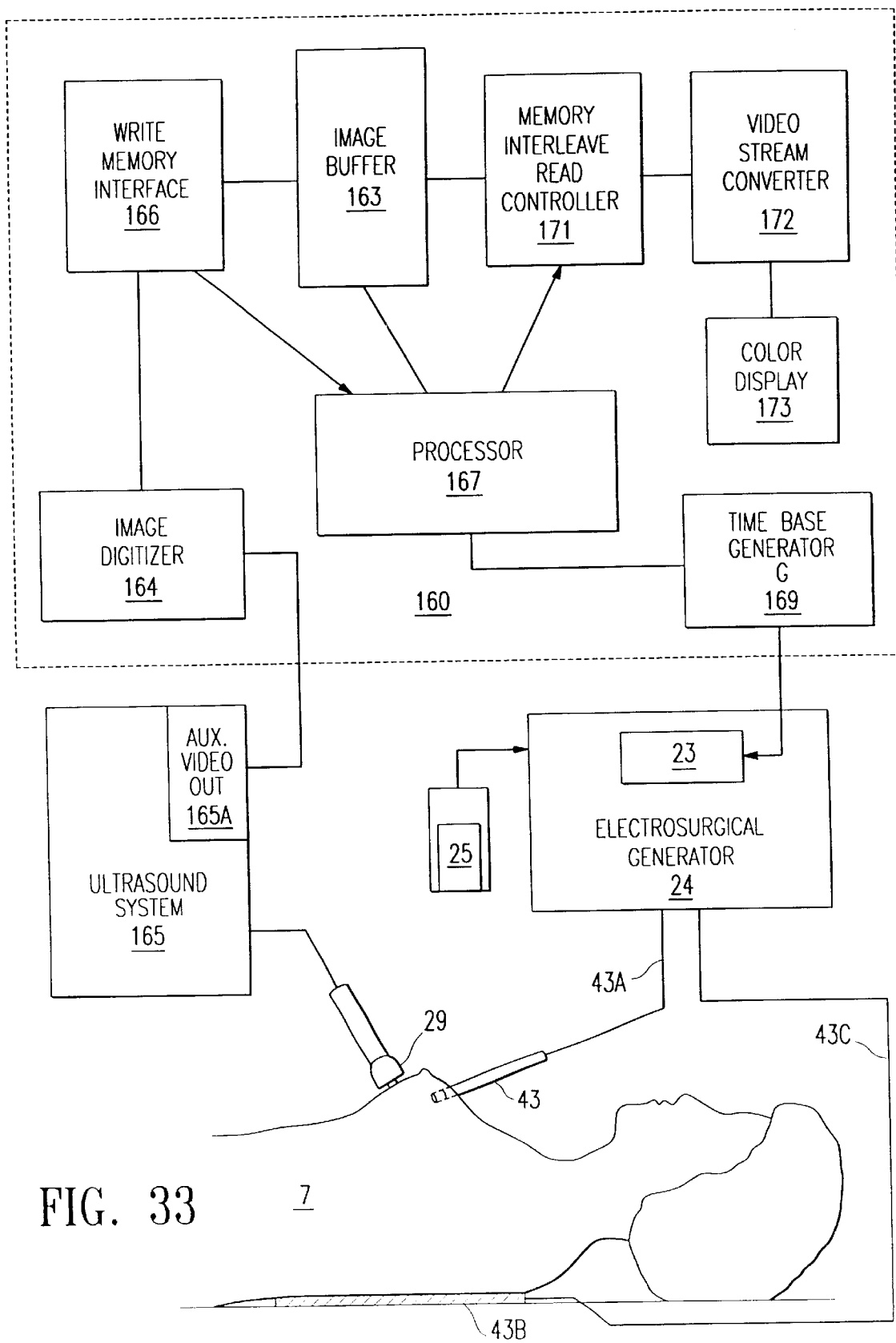
FIG. 33 shows a side elevational view of a patient and a schematic block diagram of an ultrasonic imaging system, an electrosurgical instrument, and an embodiment of an interference reduction system having features of the invention.
Figure 35:
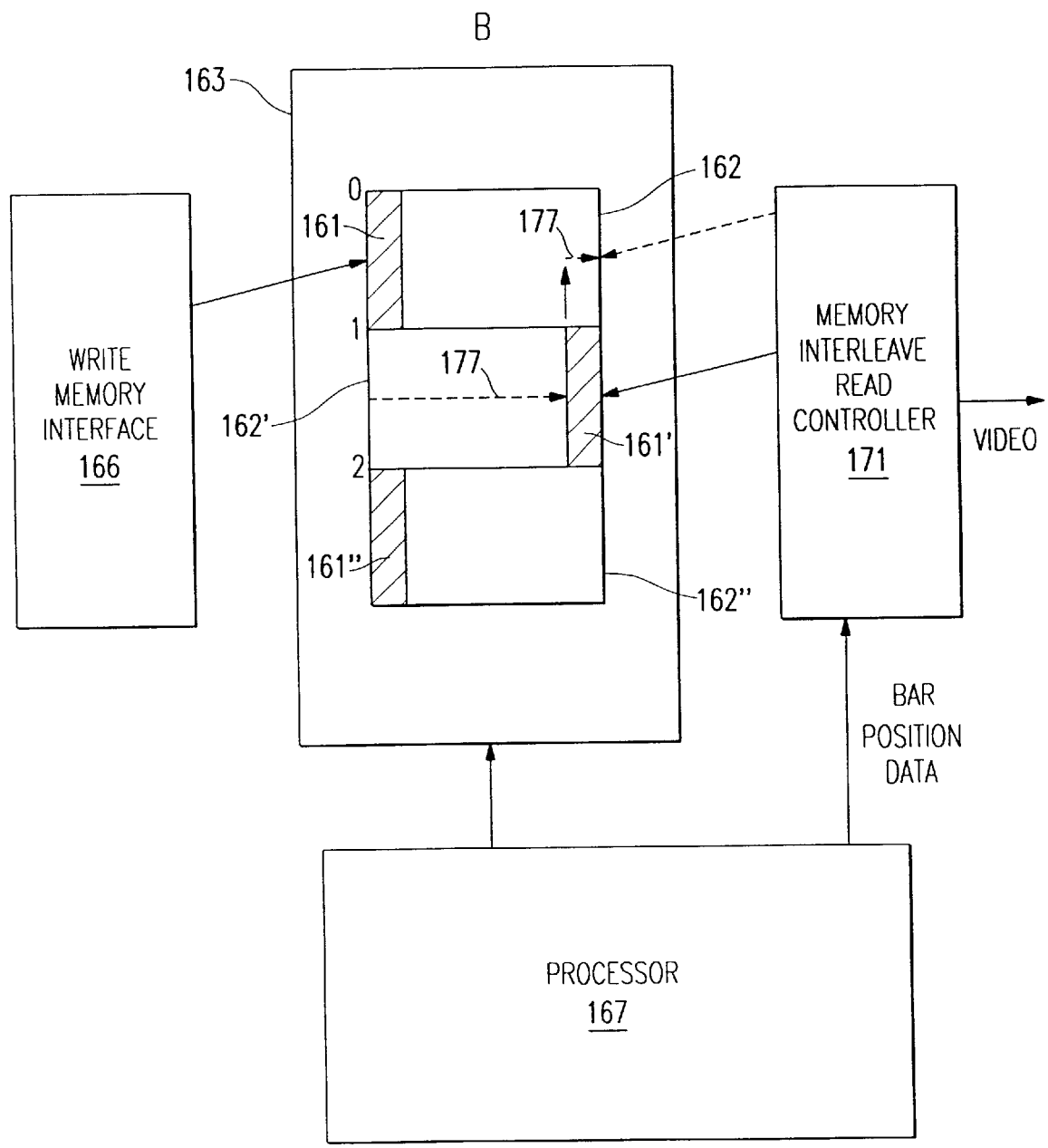
FIG. 35 is a more detailed block diagram of video buffer element B and processor F shown in FIG. 33.

Another alternative embodiment of an ultrasound interference reduction system 160 having features of the invention is shown in FIG. 33. The interference reduction system 160 of FIG. 33 can operate in a manner similar to that of the interference reduction system 140 shown in FIG. 30. The embodiment of FIG. 33, however, is also configured to replace interference scrambled portions 161, as shown in FIG. 35, of an image frame 162 stored in an image buffer 163 with portions of an adjacent or near adjacent image frame which has a corresponding portion which is clear of interference 161. The interference reduction system 160 has an image digitizer 164 which receives a video stream signal from the auxiliary video outport 165A of ultrasound system 165. The image digitizer 164 digitizes the video stream signal into digital image frames 162 and stores the digitized image frames 162 to the image buffer 163 through a write memory interface 166. The stored digitized image frame 162 moves through the ring buffer system of the image buffer 163 and can be accessed by a processor 167 therein. As the stored image frame 162 moves through the image buffer 163, the processor 167 analyzes the image to detect the position and velocity of any interference bar present therein.

The detection of an interference bar by processor 167 can be carried out in a similar fashion to that of the interference reduction system 140 shown in FIG. 30. In one embodiment, the processor 167 examines the entire stored image frame 162 pixel by pixel. In another embodiment, the image frame 162 can be scanned along scan lines defined by interference analysis zones that extend horizontally across the stored image frame 162 in a manner similar to that discussed above with regard to system 140. The processor 167 then uses the information regarding the position and velocity of the interference bar to adjust the frequency and phase of the ESG 24 operation.

The ESG 24 is coupled to a time base generator 169 which is in turn in communication with the processor 167. As an image frame 162 is ready to be output from the image buffer 163, the memory interleave read controller 171 is instructed by the processor 167 as to the location of interference bars within the stored image frame 162. As the memory interleave read controller 171 scans across the stored image frame 162, sending the image data to a video stream converter 172, it can skip up or down within the image buffer 163 to adjacent image frames 162 to corresponding clear portions of those adjacent or near adjacent image frames. Thus, an image frame 162 clear of interference 161 is synthesized from the image frame 162 of interest and clear portions of adjacent or near adjacent image frames 162 in the image buffer 163.

Figure 34:
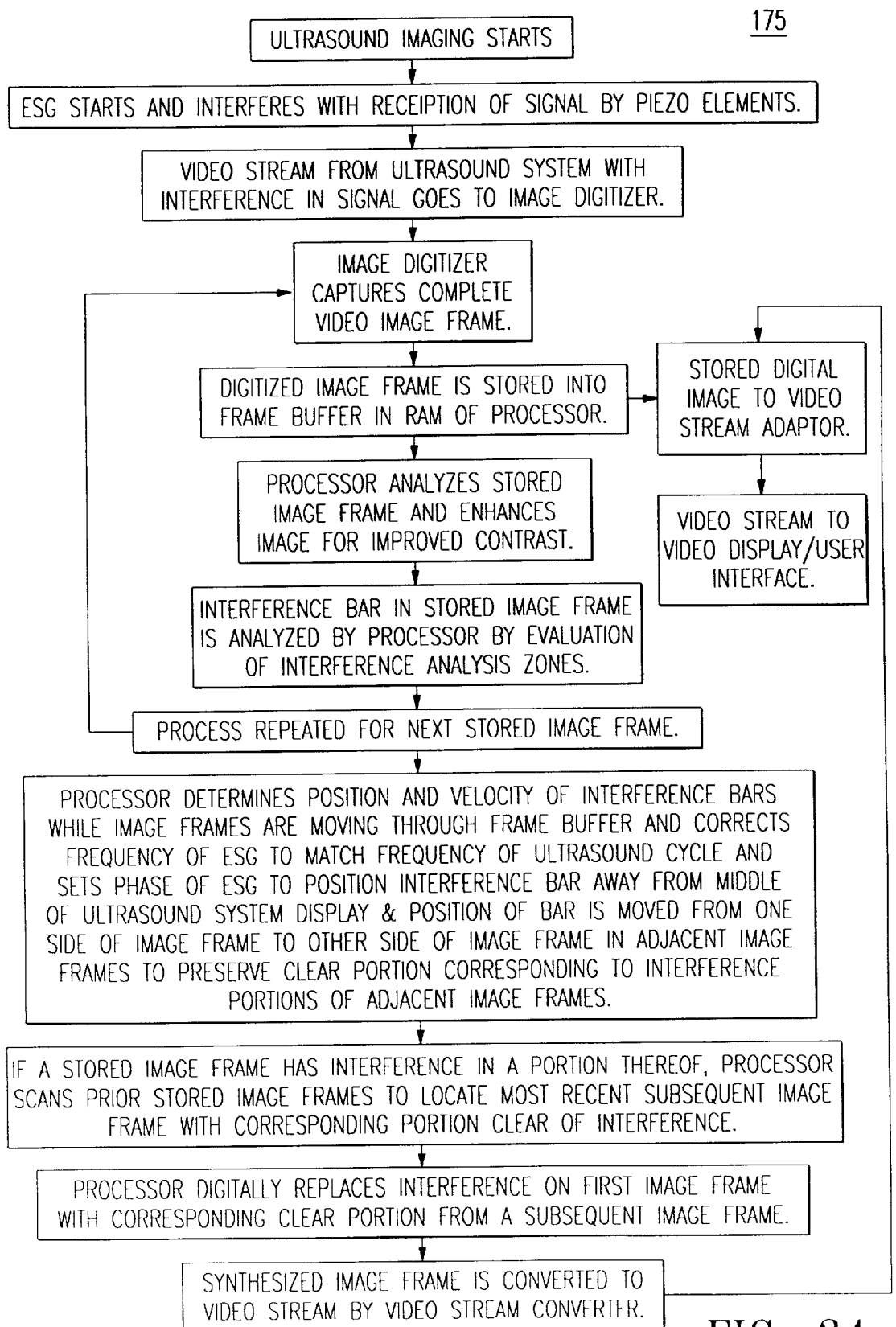
FIG. 34 is a flowchart of some of the processes of the embodiment of the invention illustrated in FIG. 33 for adjusting the frequency and phase of the intermittent operation of an electrosurgical generator in order to fix the position of an interference bar in a desired location within an image frame and to replace interfered portions of an image frame to be displayed with a corresponding portion of an adjacent image frame which is clear of interference.

An embodiment of this process is described in the flow chart 175 of FIG. 34 and shown graphically in FIG. 35. FIG. 35 shows a more detailed view of the image buffer 163 in FIG. 33 and illustrates an optional method that can be used to facilitate the replacement of interference scrambled portions 161 of a given image frame 162 with corresponding clear portions of adjacent frames 163. Specifically, FIG. 35 shows 3 sequential image frames 162, 162' and 162" in the image buffer 163. Each of the image frames 162, 162' and 162' has an interference scrambled portion 161, 161' and 161".

However, instead of the scrambled interference portions 161, 161' and 161" appearing in the same relative position within each consecutive image frame 162, 162' and 162", as is shown in the series of image frames illustrated in FIGS. 9 and 10, the processor 167 has manipulated the frequency and phase of the ESG operation in order to flip the location of the interference bar 161 from one side of the image frame 162 to the opposite side of the image frame 162' and back again in image frame 162". By this method, the read controller 171 is never required to go back in time more than one image frame 162 in order to locate a clear portion of an image frame 162 corresponding to an interference scrambled portion 161, 161' or 161" of an image frame 162, 162' or 162". This holds true so long as the duty cycle and period of the ESG 24 interferes with less than fifty percent of the image frames 162. If an interference bar occupies more than fifty percent of the image frames, more than two image frames would be required to synthesize an image frame clear of displayed interference. An alternative to replacing interference scrambled portions of an image frame with clear corresponding portions of an adjacent image frame is to first operate or gate the ESG 24 so that the period of ESG 24 operation corresponds substantially to the period of an imaging cycle. Then the phase of ESG 24 operation can be controlled so as to interfere with one complete image frame and then cease operation of the ESG 24 for the entire subsequent imaging cycle to produce an image frame clear of interference. The processor 167 can then replace the image frame that is completely obliterated by interference with the previous image frame which is clear of interference.

Also shown in FIG. 35 is a scan line 177 of the memory interleave controller 171 as it scans across the image frame 162 outputting image frame data to the video stream converter 172 and skips up to an adjacent image frame 162 in order to find a clear corresponding portion of the interference scrambled portion 161 of the image frame 162' as instructed by the processor 167. The image frame data is converted to a video stream data signal and then displayed on color display monitor 173. Color display monitor 173 can be a separate monitor that is part of the invention, or the monitor 173 may be part of the ultrasound system 165. Some of the ultrasound imaging systems 165 currently being used have input ports that allow display of externally produced video stream data.

Figure 36:
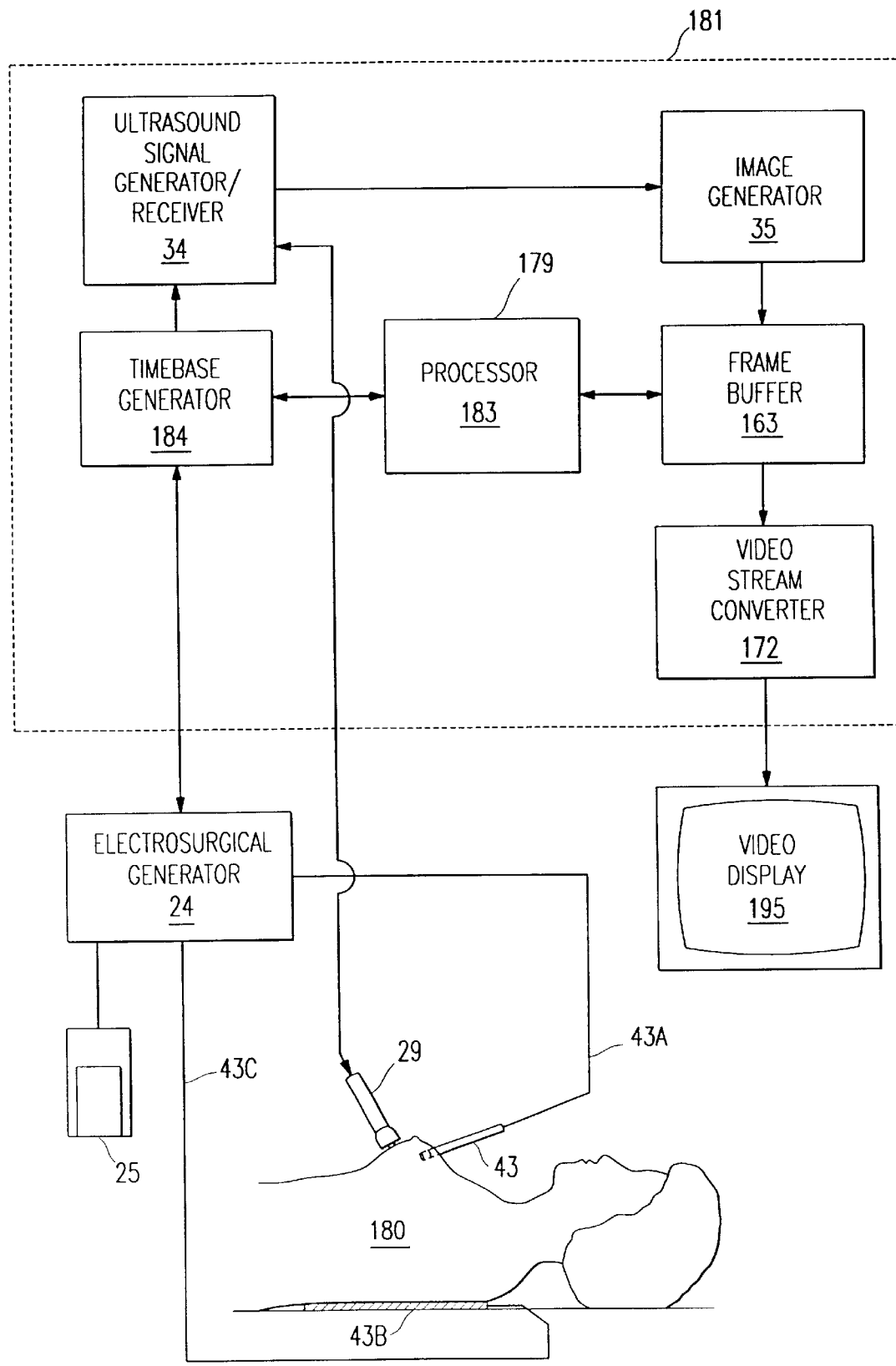
FIG. 36 shows a schematic block diagram of a patient, an ultrasonic imaging system, an electrosurgical instrument, and an embodiment of an interference reduction system having features of the invention.

FIG. 36 shows a schematic block diagram of an interference reduction system 179, a patient 180, an ultrasonic imaging system 181, and an ESG 24. The embodiment of the interference reduction system 179 of the present invention has been incorporated into the ultrasonic imaging system 181. In this system 179, there is no need for the processor 183 to measure the position and velocity of an interference bar in video stream data. The same time base generator 184 which determines the ultrasound imaging cycle of the ultrasonic imaging system 181 can be instructed by an internal processor 183 to initiate the gating sequence of the ESG 24 or other energy emitting instrument. In other words, the internal processor 183 merely sets the frequency and phase of the ultrasound imaging cycle and the ESG 24 operation to predetermined desired parameters. The processor 183 thereby proactively controls the position and velocity of any interference bar generated by the ESG 24 because the same processor 183 is controlling both the ESG 24 cycle and the ultrasound imaging cycle through the same time base generator 184 simultaneously. Alternatively, the processor 183 of the ultrasonic imaging system 181 could be configured to detect the presence of intermittent interference prior to initiating an imaging cycle. If interference energy is detected, the processor 183 can delay the beginning of an imaging cycle or gate the imaging cycle so as to position then intermittent interference in a desired portion of any given image frame produced by the ultrasonic imaging system 181.

Figure 37:
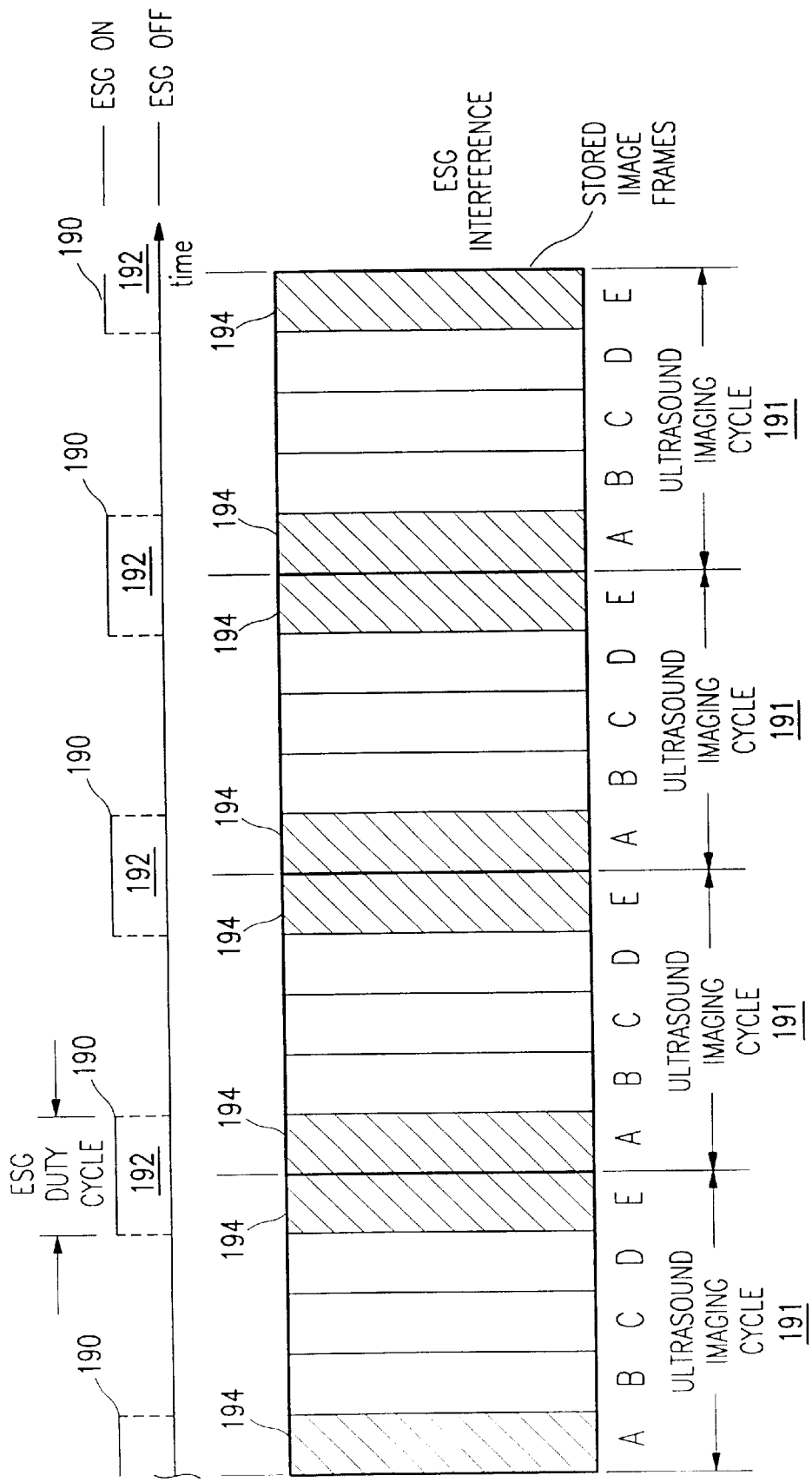
FIG. 37 is a graphical view of the chronology of intermittent ESG operation which has been synchronized with the frequency of an ultrasonic imaging cycle and phased to operate only at intervals which overlap the end and beginning of consecutive imaging cycles. The corresponding video display could be similar to that shown in FIG. 10.

FIG. 37 is a graphical view of the chronology of intermittent ESG 24 operation 190 which has been synchronized with a frequency of an ultrasonic imaging cycle 191 and phased to operate only at intervals 192 which overlap the end and beginning of consecutive imaging cycles 191 by the processor 183. The corresponding video display could be similar to that shown in FIG. 10. In addition, in the present embodiment, the processor 183 can set the position of the interference bar 194 to flip flop back and forth in alternating image frames 162 as shown in FIG. 35 so that the same image synthesis and replacement of interference scrambled portions 161 can be carried out in a frame buffer 163 so as to eliminate any perceived ESG 24 interference displayed on the video display 195.

In use, the ultrasonic imaging system 181 can operate similarly to ultrasonic imaging system 10 shown in FIG. 1, the function of which is explained in FIGS. 2–10 and the corresponding written description. As used herein, like reference numerals are used to identify like embodiments of portions of the invention which may function as previously described. Throughout the specification, processor 183 instructs the timebase generator 184 to initiate an ultrasonic imaging cycle which is carried out by sending an electrical signal from the ultrasound signal generator/receiver 34 to the transducer 29. The transducer 29 emits an ultrasonic signal into patient 180 which is subsequently reflected back and converted back into an electrical signal which is transmitted back to the ultrasound signal generator/receiver 34 in receiver mode.

The signal is then communicated from the ultrasound signal generator/receiver to the image generator wherein the reflected data is converted into a digitized image frame. The digitized image frame is then sent to an optional frame buffer 163. As discussed above, the digitized image frames can be manipulated and synthesized within the frame buffer 163 by the processor 183 to replace interference scrambled portions 161 with corresponding portions of adjacent image frames which are clear of interference. This process can be carried out as illustrated and described in FIGS. 33–35 and the corresponding written description. Any portions of the invention described with regard to the embodiment of FIGS. 33–35 necessary for carrying out the above described process, could also be used in the embodiment of FIGS. 36 and 37.

The digitized image frames are sent from the frame buffer 163 to the video stream converter 172 where the image frames are then converted to a video data stream which is then displayed on video display 195. During the above described imaging process, the processor 183 is also controlling the timebase generator 184 to gate or pulse the operation of ESG 24. The gating of the ESG 24 can be carried out as described above with regard to the embodiment of the invention in FIGS. 1, 30 and 33.

The gating can be controlled by the processor 183 in order to position the interference bar created by the ESG 24 operation into any desired portion of the image frame generated during use of the ESG 24. Thus, the interference bar could be split and fixed into position within sequential image frames so that corresponding displayed interference appears only in the lateral margins of video display 195. Also, the interference bar can be flipped from one side of the image frame to the other in order to facilitate replacement of interference scrambled portions of the image frame with corresponding portions of adjacent or near adjacent image frames which are clear of interference.

While particular forms of the invention have been illustrated and described, it will be apparent that various modifications can be made without departing from the spirit and scope of the invention. Accordingly, it is not intended that the invention be limited to the specific embodiments illustrated.

What is claimed is:

1. A method of managing intermittent interference generated by an energy emitting instrument having periods of operation and imposed upon an imaging system during operation of the imaging system comprising gating the intermittent interference to position the display of interference scrambled portions of the imaging system data within a desired portion of a display screen by gating frequency and phase of the operation periods of the energy emitting instrument.

2. The method of claim 1 wherein the energy emitting instrument comprises an electrosurgical probe.

3. The method of claim 1 wherein the imaging system comprises an ultrasonic imaging system.

4. The method of claim 1 wherein the desired portion of the display comprises the middle of a display screen.

5. The method of claim 1 wherein the desired portion of the display comprises a lateral edge of a display screen.

6. A method of managing intermittent interference imposed upon an imaging system during operation of the imaging system, comprising,
  a) storing at least a first and second image frame produced by the imaging system into a frame buffer of an interference reduction system;
  b) replacing an interference scrambled portion of the first image frame with a corresponding second image frame portion that is clear of interference to produce a synthesized image frame, comprising a combination of portions of said first and said second image frames, that is substantially clear of interference.

7. The method of claim 6 further comprising displaying the synthesized image frame on a video display monitor.

8. The method of claim 6 wherein the first and second image frames are temporally sequential in the frame buffer.

9. The method of claim 6 wherein the first image frame temporally precedes the second image frame.

10. The method of claim 6 wherein the second image frame temporally precedes the first image frame.

11. The method of claim 6 wherein the scrambled interference portion of the first image frame comprises an interference bar and the intermittent interference is generated by an energy emitting instrument.

12. The method of claim 11 further comprising gating the energy emitting instrument in frequency and phase to position the interference bar of the image frame into a desired location within the image frame prior to replacing the interference bar of the first image frame with a corresponding second image frame portion that is clear of interference.

13. The method of claim 11 wherein the energy emitting instrument is an electrosurgical probe.

14. The method of claim 6 wherein the imaging system comprises an ultrasonic imaging system.

15. An interference reduction system for managing intermittent interference from an energy emitting instrument imposed on an imaging system, comprising:
  a) a sync detector configured for communication with the imaging system;
  b) an interference bar detector in communication with the imaging system;
  c) a processor in communication with the sync detector and interference bar detector configured to calculate the position of an interference bar disposed within imaging system data from data collected by the interference bar detector; and
  d) a gating and time base generator in communication with the processor and configured for communication with and gating of the energy emitting instrument so as to gate the energy emitting instrument to position the interference bar within a desired location within imaging system data.

16. The interference reduction system of claim 15 wherein the energy emitting instrument comprises an electrosurgical probe.

17. The interference reduction system of claim 15 wherein the imaging system comprises an ultrasonic imaging system.

18. The interference reduction system of claim 15 wherein the imaging system data comprises an image frame.

19. The interference reduction system of claim 18 wherein the interference bar detector comprises a frame buffer in communication with the processor and the processor is configured to analyze pixels in a desired region of the image frame to determine whether an interference bar exists within the image frame.

20. The interference reduction system of claim 18 wherein the processor is configured to gate the energy emitting instrument during periods of an imaging cycle corresponding to a desired portion of the image frame.

21. The interference reduction system of claim 20 wherein the desired portion of the image frame comprises a lateral edge of the image frame.

22. The interference reduction system of claim 15 wherein the interference bar detector comprises a video monitor having a screen and a plurality of optical sensors in optical communication with the screen.

23. The interference reduction system of claim 22 wherein the optical detectors comprise photodiodes mounted in at least one linear array on the screen of the video monitor.

24. The interference reduction system of claim 22 further comprising an image enhancer disposed between and in electrical communication with the imaging system and video monitor.

25. The interference reduction system of claim 15 further comprising an ultrasonic imaging system having:
   a) an ultrasonic transducer;
   b) an ultrasound signal generator/receiver in communication with the ultrasound transducer and capable of transmitting an electrical signal to the transducer and receiving an electric signal produced by the reflected ultrasonic signal;
   c) an image generator capable of converting the electric signal generated from the reflected ultrasound signal into an image frame; and
   d) a video monitor in communication with the image generator system for displaying the image frame.

26. The interference reduction system of claim 15 wherein the processor is configured to gate the energy emitting instrument to operate for up to 50 percent of an imaging cycle.

27. An interference reduction system for managing intermittent interference from an energy emitting instrument imposed on an imaging system, comprising:
   a) an image digitizer configured for electrical communication with the imaging system;
   b) a processor which is in communication with the image digitizer, which has a frame buffer configured to store at least two image frames and which is configured to replace an interference scrambled portion of a first image frame stored in the frame buffer with a corresponding portion clear of interference from a second image frame stored in the frame buffer; and
   c) a counter timer in communication with the processor and configured to be electrically coupled to and gate the energy emitting instrument.

28. The interference reduction system of claim 27 wherein the energy emitting instrument comprises an electrosurgical probe.

29. The interference reduction system of claim 27 wherein the imaging system comprises an ultrasonic imaging system.

30. The interference reduction system of claim 27 further comprising an ultrasonic imaging system having:
   a) an ultrasonic transducer;
   b) an ultrasound signal generator/receiver in communication with the ultrasound transducer and capable of transmitting an electrical signal to the transducer and receiving an electric signal produced by the reflected ultrasonic signal;
   c) an image generator capable of converting the electric signal generated from the reflected ultrasound signal into an image frame; and
   d) a video monitor in communication with the image generator system for displaying the image frame.

31. The interference reduction system of claim 30 wherein the processor is configured to gate the energy emitting instrument during periods of an imaging cycle corresponding to a desired portion of the image frame which alternates position within sequential image frames.

32. The interference reduction system of claim 27 wherein the processor is configured to gate the energy emitting instrument to operate for up to 50 percent of an imaging cycle.

* * * * *